(12) United States Patent
Pitner et al.

(10) Patent No.: US 8,455,703 B2
(45) Date of Patent: Jun. 4, 2013

(54) USE OF IONIC LIQUIDS WITH TETRACYANOBORATE ANIONS AS A SOLVENTS FOR EXTRACTION OF ALCOHOLS FROM AQUEOUS SOLUTIONS

(75) Inventors: William-Robert Pitner, Frankfurt (DE); Michael Schulte, Bischofsheim (DE); Andrzej Górak, Witten (PL); Francesca Santangelo, Dortmund (IT); Annebart Engberg Wentink, Mannheim (NL)

(73) Assignee: Merck Patent GmbH, Darmstadt (DE)

( * ) Notice: Subject to any disclaimer, the term of this patent is extended or adjusted under 35 U.S.C. 154(b) by 290 days.

(21) Appl. No.: 12/993,903

(22) PCT Filed: May 15, 2009

(86) PCT No.: PCT/EP2009/003485
§ 371 (c)(1),
(2), (4) Date: Nov. 22, 2010

(87) PCT Pub. No.: WO2009/152906
PCT Pub. Date: Dec. 23, 2009

(65) Prior Publication Data
US 2011/0071324 A1 Mar. 24, 2011

(30) Foreign Application Priority Data

May 26, 2008 (EP) .................................. 08009552
Sep. 9, 2008 (EP) .................................. 08015819

(51) Int. Cl.
*C07C 29/86* (2006.01)
(52) U.S. Cl.
USPC ......................................... 568/918; 568/913
(58) Field of Classification Search
USPC ....................................................... 568/918
See application file for complete search history.

(56) References Cited

U.S. PATENT DOCUMENTS

2006/0222584 A1* 10/2006 Welz-Biermann et al. ... 423/377

FOREIGN PATENT DOCUMENTS

| DE | 102006024397 B3 | 10/2007 |
| WO | 2004007289 A1 | 8/2004 |
| WO | 2010000357 A2 | 1/2010 |

OTHER PUBLICATIONS

Database CAPLUS on STN, Acc. No. 2008:586963, Izak et al., Chemical Engineering Journal (2008), 139(2), p. 318-321 (abstract).*
World IP Organization. "International Search Report." PCT/EP2009/003485, Applicant: Merck Patent Gesellschaft, Mailed: Mar. 1, 2010.
Fadeev, Andrei G. and Michael M. Meagher. "Opportunities for ionic liquids in recovery of biofuels." (Chem. Community), Jan. 23, 2001, pp. 295-296.
Freemantle, Michael. "Ionic Liquids in a Renewable Ferment." (Science & Technology), Apr. 2, 2001, vol. 79, No. 14.
Izak, Pavel et al. "Increased productivity of *Clostridium acetobutylicum* fermentation of acetone, butanol, and ethanol by pervaporation through supported ionic liquid membrane." (Biotechnological Products and Process Engineering), Jan. 29, 2008, pp. 597-602, No. 78.
Chapeaux, Alexandre et al. "Liquid Phase Behavior of Ionic Liquids with Water and 1-Octanol and Modeling of 1-Octanol/Water Partition Coefficients." (Journal of Chem. Eng. Data), 2007, pp. 2462-2467, No. 52.
Espacenet Database: "English Abstract—Multiphase-membrane, useful e.g. for extracting hydrophilic substances e.g. carbohydrate, comprises an ionic fluid, where the membrane is doubly coated with a coating material based on silicon or siloxane." DE102006024397B3, Applicant: Universitaet Rostock, Oct. 11, 2007.

* cited by examiner

*Primary Examiner* — Brian J Davis
(74) *Attorney, Agent, or Firm* — Millen, White, Zelano & Branigan, P.C.

(57) ABSTRACT

The invention relates to a method for the liquid-liquid extraction of alcohols from aqueous solutions using at least one ionic liquid containing a tetra-cyanoborate anion as solvent.

15 Claims, 14 Drawing Sheets

USE OF IONIC LIQUIDS WITH TETRACYANOBORATE ANIONS AS A SOLVENTS FOR EXTRACTION OF ALCOHOLS FROM AQUEOUS SOLUTIONS

The invention relates to a method for the liquid-liquid extraction of alcohols from aqueous solutions using at least one ionic liquid containing a tetra-cyanoborate anion as solvent.

The extraction of alcohols from aqueous solutions is increasing more and more in importance due to intense debate about "white biotechnology" or the use of alcohols as additives to conventional fuels. As part of the intense debate about biofuels, in particular bioethanol, it has emerged that biobutanol, i.e. butanol prepared from biomass, is likewise of interest as potential biofuel.

Biobutanol has a number of advantages over other biofuels, in particular
owing to the low vapour pressure (5.6 hPa compared with 58.5 hPa in the case of ethanol) and the relatively low flash point (36° C. compared with 12° C. for ethanol), it can easily be mixed with conventional fuels,
it exhibits significantly less hygroscopic behaviour,
the energy content is similar to that of conventional fuels,
it is, for example, less corrosive,
it can replace fossil fuels to the extent of 100% without the need for engine modifications and
it can be mixed with biodiesel/diesel and used in diesel engines.

The preparation of alcohols from biomass has been known for some time. A fermentation which was already employed industrially in the first half of the twentieth century is ABE fermentation (acetone-butanol-ethanol fermentation). At that time, the microorganism *Clostridium acetobutyricum* was employed. Nowadays, further bacteria from the *Clostridium* genus, such as, for example, *C. beijerinckii, C. saccharoperbutylacetonicum* and *C. tetanomorphum*, are employed for the preparation of butanol from biomass. In addition, new microorganisms, in particular bacteria and yeasts, are being developed which produce a higher butanol proportion and in addition are also more tolerant to butanol in the fermentation solution. However, the tolerance limit is as low as 2 per cent by weight of butanol, based on the aqueous solution.

The extraction of alcohols, in particular butanol, from an aqueous solution, and in a particular embodiment the purification of fermentation broths, therefore continues to be a challenge. The removal of alcohols from aquaous solutions by distillation is expensive. Owing to the higher boiling point of butanol compared with water, rectification cannot be carried out economically as a separation method for butanol. Extraction methods used to date require extraction media which are generally flammable, environmentally harmful or toxic.

For the extraction of alcohols from fermentation broths, the fatty alcohol oeyl alcohol is currently being investigated the most frequently. However, this has the disadvantage of being an emulsifier, which may result in foaming on use in liquid-liquid extraction. The formation of a foam phase results in a greater loss of pressure in extraction columns and in addition makes phase separation of the two liquid phases more difficult. In addition, oleyl alcohol is classified as "irritating to respiratory system".

There is therefore a demand for novel extraction media for the extraction of alcohols from aqueous solutions which can be employed as an alternative to conventional compounds and which have a high distribution coefficient and high selectivity for the alcohol to be extracted. The requirements of the novel media are therefore:
good selectivity for the uptake of the alcohol to be extracted, ideally having a selectivity coefficient>100,
good distribution coefficient, for example having a distribution coefficient $D_{alcohol}$>2,
immiscible with water,
low water uptake by the aqueous solution,
non-toxic to the microorganism if the aqueous solution is a fermentation broth.

The object of the present invention is accordingly to provide novel extraction media for the liquid-liquid extraction of alcohols from aqueous solutions.

This object is achieved in accordance with the invention by the features of the main claim and the co-ordinate claims.

Surprisingly, it has been found that ionic liquids containing tetracyanoborate anions are particularly suitable as solvents for liquid-liquid extraction of this type of alcohols from aqueous solutions.

The invention therefore relates to a method for the liquid-liquid extraction of alcohols from aqueous solutions using at least one ionic liquid containing tetracyanoborate anions as solvent.

The ionic liquid containing tetracyanoborate anions ideally has the property of forming a two-phase mixture with the aqueous solution comprising at least one alcohol.

The invention therefore furthermore relates to a method for the liquid-liquid extraction of alcohols from aqueous solutions using at least one ionic liquid containing a tetracyanoborate anion as solvent, characterised in that the ionic liquid containing tetracyanoborate anions forms at least one two-phase mixture with the aqueous solution comprising at least one alcohol.

The ionic liquids containing tetracyanoborate anions and the preparation and uses thereof as solvents for many synthetic or catalytic reactions, for example Friedel-Crafts acylation and alkylation, Diels-Alder cycloadditions, hydrogenation and oxidation reactions, Heck reactions, as precursors for the preparation of liquid-crystal compounds and of active compounds, inter alis for medicaments and crop-protection compositions, or as non-aqueous electrolyte, optionally in combination with other known electrolytes, or as phase-transfer catalyst or as medium for the heterogenisation of homogeneous catalysts, are disclosed, for example, in WO 2004/072089.

The use of tetrapropylammonium tetracyanoborate as constituent of a multiphase membrane for use in an industrial membrane method for the purification of liquid mixtures, so-called pervaporation, is disclosed in DE 10 2006 024 397. Liquid mixtures described are carbohydrates or alcohols in aqueous solutions. The physical processes occurring in the membrane material can be described by means of the solution-diffusion model. According to the model idea, one component of the mixture to be separated preferably penetrates into the membrane and is adsorbed on its inner surface or dissolved in the entire membrane material. The concentration of the readily soluble component becomes lower towards the outside of the membrane, since it evaporates at the membrane surface and is thus continuously removed. A concentration gradient thus becomes established over the membrane cross section, acting as driving force for the diffusion of the permeate through the membrane.

In contrast to the pervaporation method described, the method according to the invention is a liquid-liquid extraction. In liquid-liquid extraction, in which two liquid phases are involved, the valuable product, in this case the alcohol, is transferred from the support phase into the extract phase. A phase equilibrium with respect to the concentration of valuable product becomes established between the two phases in accordance with the Nernst distribution law:

$$D_{alcohol} = \frac{C_{alcohol}^{IL}}{C_{alcohol}^{AQ}}$$

$D_{alcohol}$=Nernst distribution coefficient for the Valuable product, here alcohol $C_{alcohol}^{IL}$: concentration of the valuable product, here alcohol, in the ionic liquid $C_{alcohol}^{AQ}$: concentration of the valuable product, here alcohol, in the aqueous phase The selectivity S is defined as the quotient of the Nernst distribution coefficients of alcohol to water:

$$S = \frac{D_{alcohol}}{D_{water}}$$

Liquid-liquid extraction is a separation method in which mass transfer takes place between two liquid phases and is limited by the thermodynamic equilibrium that becomes established, in accordance with the Nernst distribution coefficient. By contrast, pervaporation is not limited by the thermodynamic equilibrium since the separation mechanism is the different transport properties of the components in the membrane. In addition, mass transfer in liquid-liquid extraction takes place between the two liquid phases, while in pervaporation it takes place between a liquid phase, a solid phase and a vapour phase. In contrast to liquid-liquid extraction, pervaporation is therefore dependent on the pressure set on the permeate side.

The liquid-liquid extraction according to the invention of alcohols from aqueous solutions using at least one ionic liquid containing tetracyanoborate anions is preferably carried out by a mthod in which a) the aqueous solution comprising at least one alcohol is provided, b) the aqueous solution from a) is mixed intensively with the at least one ionic liquid containing tetracyanoborate anions, so that the ionic liquid is able to extract at least some of the alcohol from the aqueous solution and form an at least single-phase mixture with this alcohol, c) the at least single-phase mixture from b) is separated off from the aqueous solution, d) the single-phase mixture from c) is separated into the components alcohol and ionic liquid, and optionally e) the ionic liquid from d) is fed back into step b).

The liquid-liquid extraction according to the invention, as described, can be carried out by the batch method. However, it can also be carried out continuously or semi-continuously. The liquid-liquid extraction here can be carried out by either the countercurrent, co-current or cross-current method and in one or more steps. The liquid-liquid extraction can be carried out either in a one-step or multistep mixer-settler battery or alternatively in an extraction column. The method according to the invention can be carried out in all extraction apparatuses and by all procedures known to the person skilled in the art, for example documented by the specialist literature by J. Rydberg, M. Cox, C. Muskas, G. R. Chopppin, 2004, Solvent Extraction Principles and Practice or R. H. Perry, 1984, Perry's chemical engineer's handbook.

A variant of a liquid-liquid extraction is described in FIG. 1.

The reference numbers in FIG. 1 are as follows:

[1] Reaction vessel containing the aqueous solution comprising at least one alcohol and the ionic liquid according to the invention, in particular an in-situ fermenter

[2] Recovery unit

[3] Addition of the aqueous solution comprising at least one alcohol, in particular the fermentation medium including microorganisms and ionic liquid

[4] Aqueous phase of the aqueous solution comprising at least one alcohol, in particular in the case of fermentation also the microorganisms

[5] Phase of the ionic liquid, optionally comprising the part of the extracted alcohol forming the at least single-phase mixture

[6] Stream to the recovery unit containing the phase of the ionic liquid comprising some of the extracted alcohol

[7] Extracted and separated-off alcohol

[8] Optionally discharged stream of the aqueous phase, in particular the fermentation broth

[9] Recycling of the purified ionic liquid.

In [1], the aqueous phase comprising the at least one alcohol, in particular the fermentation broth comprising fermentation medium and microorganisms, is brought into contact and mixed with the ionic liquid. In the case of the preferred embodiment of fermentation, the fermentation, i.e. the production of the alcohol by the microorganisms, and separation of the alcohol from the fermentation broth by extraction by means of an ionic liquid take place simultaneously in [1]. After separation of the phases in [4] and [5], the ionic liquid is fed into a recovery unit [2] by means of stream [6], and the butanol is separated off and discharged in stream [7]. The regenerated ionic liquid is fed back into [1] in stream [9].

A variant of a fermentation according to the invention with the aid of an extraction column is described in FIG. 2.

The reference numbers in FIG. 2 are as follows:

[1] Fermenter

[2] Recovery unit

[3] Addition of the fermentation medium including microorganisms

[4] Fermentation broth

[5] Phase of the ionic liquid, optionally comprising the part of the extracted alcohol forming the at least single-phase mixture

[6] Aqueous phase of the aqueous solution comprising at least one alcohol

[7] Discharged aqueous phase, which may also be fed back into [1]

[8] Optionally discharged stream of the aqueous phase, fermentation broth

[9] Extraction column

[10] Stream to the recovery unit containing the phase of the ionic liquid comprising some of the extracted alcohol

[11] Extracted and separated-off alcohol

[12] Cell recycling, comprising the microorganisms and in some cases fermentation medium

[13] Cell separation unit

[14] Aqueous phase of the aqueous solution comprising at least one alcohol

[15] Addition of the ionic liquid

The fermentation broth comprising fermentation medium and microorganisms is stirred and aerated in [1]. Some of the fermentation broth is fed to the cell separation unit by means of stream [4]. The cells or microorganisms are separated in the cell separation unit [13]. The cells or microorganisms are fed back into the fermenter [1] by means of stream [12]. The separated-off aqueous solution comprising at least one alcohol is fed into the extraction column [9] by means of stream [14]. The two phases, aqueous phase comprising at least one alcohol and ionic liquid optionally comprising some of the extracted alcohol, are brought into contact in the extraction column [9]. The alcohol is extracted in the extraction column, i.e. part thereof is transferred from the aqueous phase into the ionic liquid phase. The aqueous phase is removed semi-continuously in stream [7], and some or all thereof is fed back into [1]. The phase of the ionic liquid comprising some of the extracted alcohol is fed into a recovery unit by means of stream [10]. The alcohol is separated off from the ionic liquid in the recovery unit [2] and discharged in stream [11]. The regenerated stream [8], the regenerated ionic liquid comprising no alcohol, is fed back into the extraction column [9].

In general, the term alcohol in the sense of the invention encompasses both monohydroxyalcohols, preferably having 2, 3 or 4 C atoms, and alcohols containing more than one hydroxyl group, for example diols, preferably having 3, 4 or 5 C atoms.

Selected diets are, for example, 2,3-butanediol and 1,3-propanediol.

In a preferred embodiment of the invention, the at least one alcohol is selected from the group ethanol, isopropanol, propanol, n-butanol or isomers of n-butanol, or mixtures thereof. The method according to the invention is particularly preferably used for the extraction of n-butanol, isomers of n-butanol or mixtures thereof. The method according to the invention is very particularly preferably used for the extraction of n-butanol.

The so-called biobutanol prepared by fermentation comprises n-butanol as principal component and isomeric butanols as secondary constituents. The term n-butanol is equivalent to 1-butanol. The use of the term butanol should be regarded as identical to n-butanol below.

The aqueous solution in the method according to the invention comprises the alcohol in a concentration of 0.01 to 50 per cent by weight, preferably in a concentration of 0.1 to 30 per cent by weight, particularly preferably in a concentration of 0.5 to 10 per cent by weight, based on the aqueous solution. For aqueous solutions from biomass, i.e. for fermentation broths, the alcohol is present in a concentration of 0.1 to 3 per cent by weight, preferably in a concentration of 0.5 to 0.2 per cent by weight, based on the fermentation broth. A natural limit is the production limit of the microorganism. However, it is also possible to concentrate the fermentation broth in advance and then to carry out the method according to the invention.

In a preferred embodiment of the invention, the aqueous solution comprising at least one alcohol is a fermentation broth, in particular a fermentation broth from an acetone-butanol-ethanol fermentation (ABE fermentation).

For ABE fermentation, the microorganism *Clostridium beijerinckii* used initially has been further developed into *Clostridium beijerinckil* BA101, which is able to produce or tolerate a butanol concentration of up to 17.8 g/l, which is more favourable compared with defined nutrient media, for example glucose corn steep liquor medium. The concentration of the glucose corn steep liquor medium is 60 g/l. Important by-products in this fermentation are acetone and ethanol with concentrations of 5.5 g/l and 1 g/l respectively. Further by-products having very low concentrations are acetic acid and butyric acid.

General, expert knowledge includes the temperature at which the liquid-liquid extraction according to the invention is carried out. In the case of the particular embodiment of the extraction of the alcohol from an in-situ fermentation, as defined below, the ideal temperature of the microorganism at which the production of the alcohol can preferably take place should, for example, be noted.

In a preferred embodiment of the present invention, the cation of the ionic liquid containing tetracyanoborate anions is hydrophobic.

The cations are preferably organic cations and particularly preferably the organic cations selected from the group comprising ammonium, phosphonium, sulfonium, uronium, thiouronium, guanidinium cations or heterocyclic cations.

From the group of the ammonium, phosphonium or sulfonium tetracyanoborates, preference is given to the compounds of the formulae (1), (2) and (3):

$[NR_4]^+[B(CN)_4]^-$         (1), $[PR_4]^+[B(CN)_4]^-$         (2), $[SR_3]^+[B(CN)_4]^-$         (3), where
R in each case, independently of one another, denotes
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 5-7 C atoms, which may be substituted by alkyl groups having 1-6 C atoms, with the proviso that at least two substituents R have at least 5 C atoms.

From the group of the uranium or thiouronium tetracyanoborates, preference is given to the compounds of the formulae (4) and (5):

$[C(R^3R^4N)(OR^5)(NR^6R^7)]^+[B(CN)_4]^-$     (4), $[C(R^3R^4N)(SR^5)(NR^6R^7)]^+[B(CN)_4]^-$     (5), where
$R^3$ to $R^7$ each, independently of one another, denote
H, where H is excluded for $R^5$,
a straight-chain or branched alkyl having 1 to 20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

From the group of the guanidinium tetracyanoborates, preference is given to the compounds of the formula (6)

$[C(NR^8R^9)(NR^{10}R^{11})(NR^{12}R^{13})]^+[B(CN)_4]^-$     (6), where
$R^8$ to $R^{13}$ each, independently of one another, denote
H,
a straight-chain or branched alkyl having 1 to 20 C atoms,
a straight-chain or branched alkenyl having 2-20 C atoms and one or more double bonds,
a straight-chain or branched alkynyl having 2-20 C atoms and one or more triple bonds,
saturated, partially or fully unsaturated cycloalkyl having 3-7 C atoms, which may be substituted by alkyl groups having 1-6 C atoms.

From the group of the tetracyanoborates having a heterocyclic cation, preference is given to the compounds of the formula (7)

$[HetN]^{z+}[B(CN)_4]^-$         (7), where
HetN^(z+) denotes a heterocyclic cation selected from the group
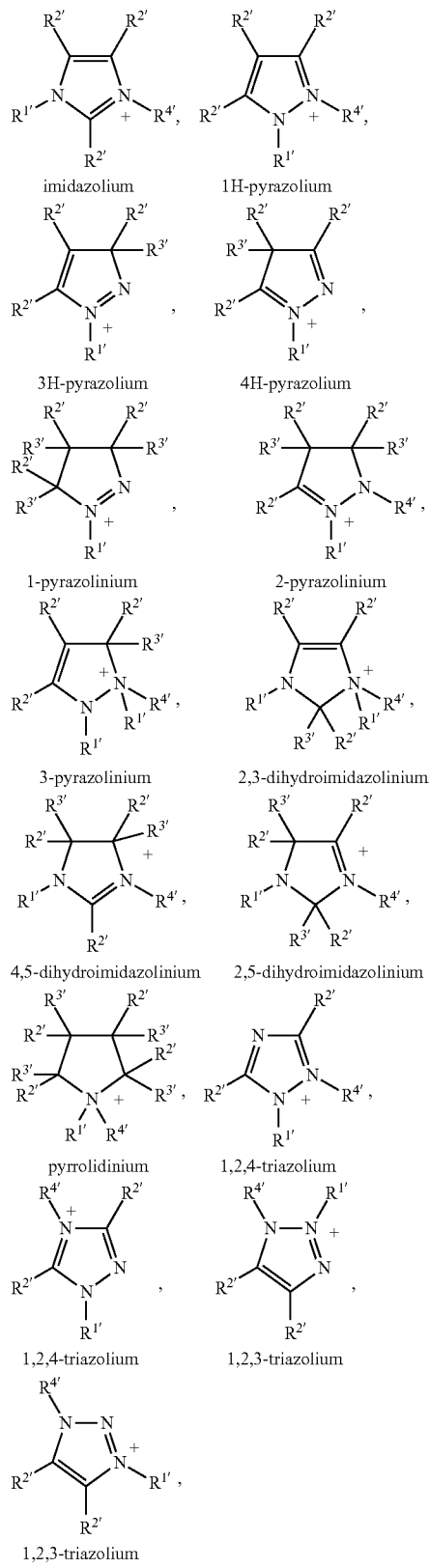
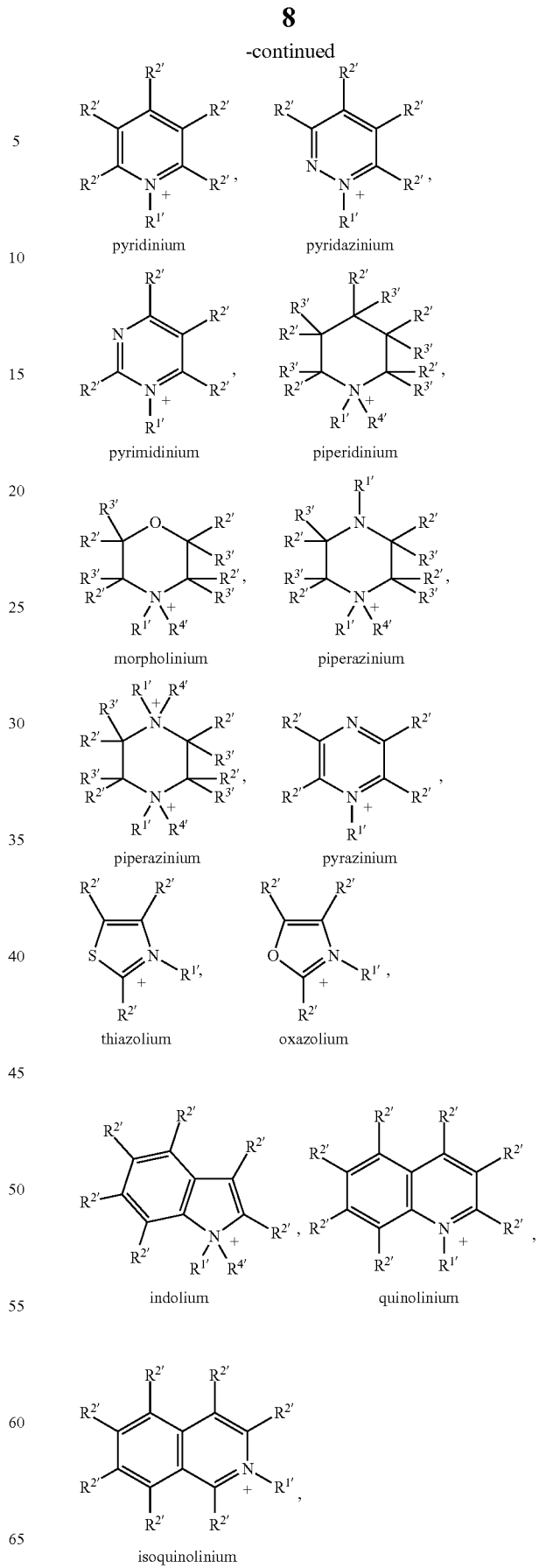

-continued

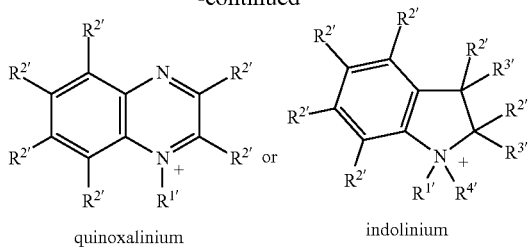

quinoxalinium     indolinium where the substituents $R^{1'}$ to $R^{4'}$ each, independently of one another, denote a straight-chain or branched alkyl having 1-20 C atoms, a straight-chain or branched alkenyl having 2-20 C atoms and one or more double bonds, a straight-chain or branched alkynyl having 2-20 C atoms and one or more triple bonds, saturated, partially or fully unsaturated cycloalkyl having 5-7 C atoms, which may be substituted by alkyl groups having 1-6 C atoms, where the substituents $R^{1'}$, $R^{2'}$, $R^{3'}$ and/or $R^{4'}$ together may also form a ring system.

For the purposes of the present invention, fully unsaturated substituents are also taken to mean aromatic substituents.

In accordance with the invention, suitable substituents R and $R^3$ to $R^{13}$ of the compounds of the formulae (1) to (6) are in each case, independently of one another, preferably $C_6$- to $C_{18}$-, in particular $C_8$- to $C_{14}$-alkyl groups.

The substituents R in the compounds of the formulae (1), (2) and (3) may be identical or different. For ammonium or phosphonium tetracyanoborates of the formulae (1) and (2), three substituents R are preferably identical and one substituent R is different. For the sulfonium tetracyanoborates of the formula (3), two substituents R are preferably identical and one substituent R is different.

The substituents R are particularly preferably pentyl, hexyl, octyl, decyl, dodecyl or tetradecyl.

Up to four substituents of the guanidinium cation $[C(NR^8R^9)(NR^{10}R^{11})(NR^{12}R^{13})]^+$ may also be bonded in pairs in such a way that mono-, bi- or polycyclic cations are formed.

Without restricting generality, examples of such guanidinium cations are:

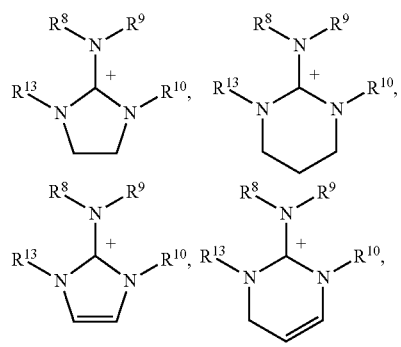

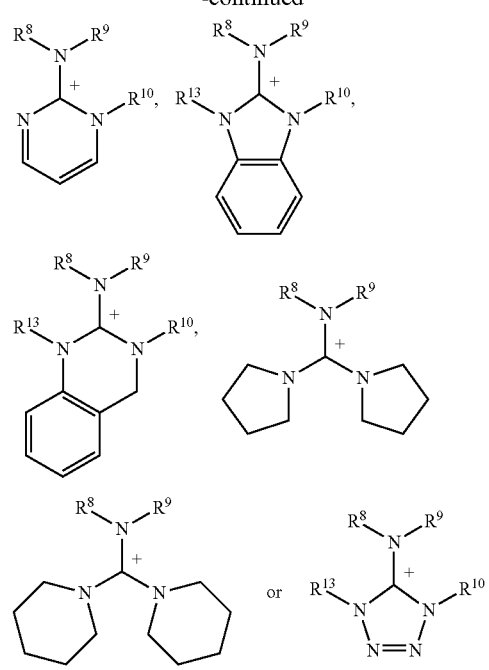

where the substituents $R^8$ to $R^{10}$ and $R^{13}$ can have a meaning or particularly preferred meaning indicated above.

If desired, the carbocycles or heterocycles of the guanidinium cations indicated above may also be substituted by $C_1$- to $C_6$-alkyl.

Up to four substituents of the uronium cation $[C(R^3R^4N)(OR^5)(NR^6R^7)]^+$ or thiouronium cation $[C(R^3R^4N)(SR^5)(NR^6R^7)]^+$ may also be bonded in pairs in Such a way that mono-, bi- or polycyclic cations are formed.

Without restricting generality, examples of such cations are indicated below where Y=O or S:

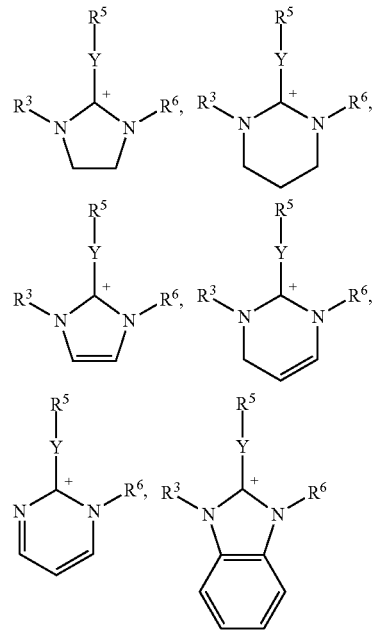

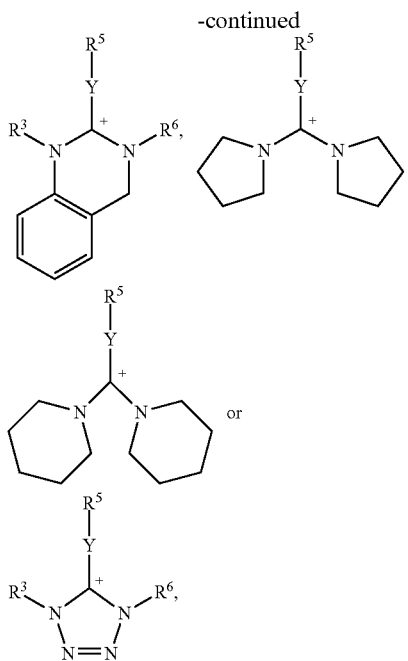

where the substituents $R^3$, $R^5$ and $R^6$ can have a meaning or particularly preferred meaning indicated above.

If desired, the carbocycles or heterocycles of the cations indicated above may also be substituted by $C_1$- to $C_6$-alkyl.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (4) to (6) may be identical or different. $R^3$ to $R^{13}$ are particularly preferably each, independently of one another, methyl, ethyl, n-propyl, isopropyl, n-butyl, tert-butyl, sec-butyl, phenyl, hexyl or cyclohexyl, very particularly preferably methyl, ethyl, n-propyl, isopropyl, n-butyl or hexyl.

In accordance with the invention, suitable substituents $R^{1'}$ to $R^{4'}$ of compounds of the formula (7), besides H, are preferably: $C_1$- to $C_{20}$-, in particular $C_1$- to $C_{12}$-alkyl groups.

The substituents $R^{1'}$ and $R^{4'}$ are each, independently of one another, particularly preferably methyl, ethyl, isopropyl, propyl, butyl, sec-butyl, tertbutyl, pentyl, hexyl, octyl, decyl, dodecyl, cyclohexyl, phenyl or benzyl. They are very particularly preferably methyl, octyl, decyl or dodecyl. In pyrrolidinium, piperidinium or morpholinium compounds, the two substituents $R^{1'}$ and $R^{4+}$ are preferably different.

The substituent $R^{2'}$ or $R^{3'}$ is in each case, independently of one another, in particular, H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, $-C_9H_{17}$, $-C_{10}H_{19}$ to $-C_{20}H_{39}$, preferably allyl, 2- or 3-butenyl, isobutenyl, sec-butenyl, furthermore preferably 4-pentenyl, iso-pentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, hept-ynyl, octynyl, $-C_9H_{15}$, $-C_{10}H_{17}$ to $-C_{20}H_{37}$, preferably ethynyl, 1- or 2-propyn-yl, 2- or 3-butynyl, 4-pentynyl, 3-pentynyl or hexynyl.

Unsubstituted saturated or partially or fully unsaturated cycloalkyl groups having 5-7 C atoms are therefore cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups.

$HetN^{z+}$ is preferably

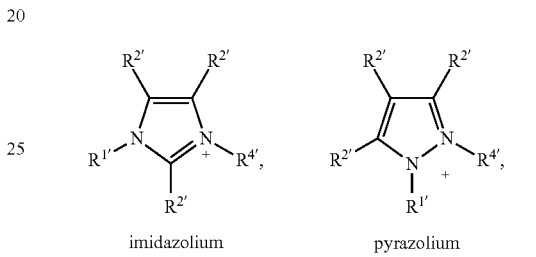

imidazolium      pyrazolium

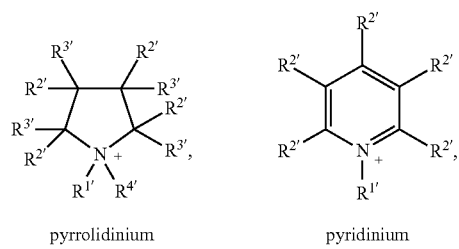

pyrrolidinium      pyridinium

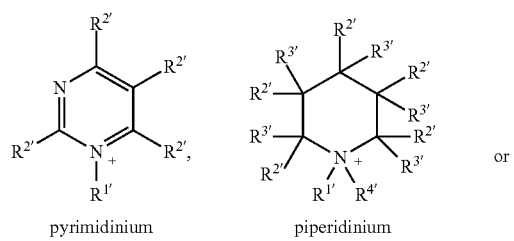

pyrimidinium      piperidinium    or

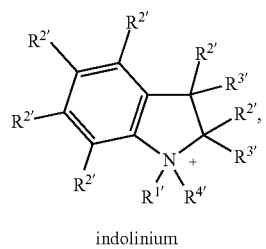

indolinium where the substituents $R^{1'}$ to $R^{4'}$ each, independently of one another, have a meaning described above.

HetN$^{z+}$ is particularly preferably

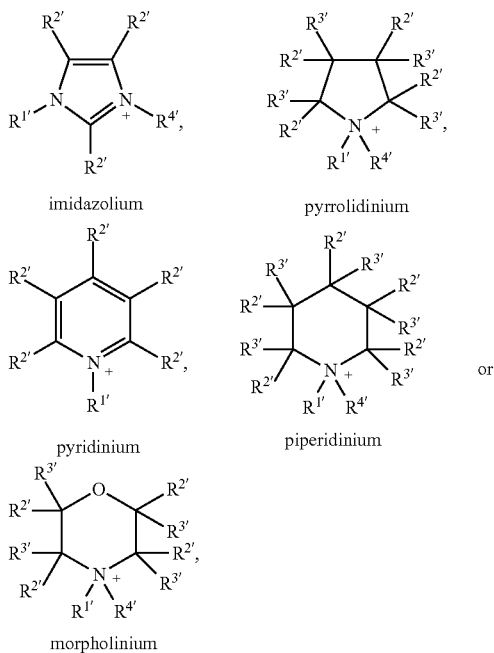

imidazolium pyrrolidinium pyridinium piperidinium morpholinium where the substituents R$^{1'}$ to R$^{4+}$ each, independently of one another, have a meaning described above.

HetN$^{z+}$ is very particularly preferably imidazolium, where the substituents R$^{1'}$ to R$^{4'}$ each, independently of one another, have a meaning described above.

In a preferred embodiment of the method, the at least one ionic liquid containing tetracyanoborate anions is selected from the group of the compounds of the formulae (1), (2) and (7), having substituents as defined or preferably defined above. Very particular preference is given to the use of compounds of the formula (7) and preferred compounds thereof, as described above.

The ionic liquids containing tetracyanoborate anions for use in the method according to the invention are particularly preferably selected from the group
1-octyl-3-methylimidazolium tetracyanoborate,
1-decyl-3-methylimidazolium tetracyanoborate,
1-dodecyl-3-methylimidazolium tetracyanoborate,
trihexyltetradecylammonium tetracyanoborate,
trihexyltetradecylphosphonium tetracyanoborate,
N-octylpyridinium tetracyanoborate,
1-octyl-1-methylpyrrolidinium tetracyanoborate,
N-octyl-N-methylmorpholinium tetracyanoborate,
1-octyl-1-methylpiperidinium tetracyanoborate.

Very particular preference is given to the use of 1-octyl-3-methylimidazolium tetracyanoborate. Very particular preference is given to the use of 1-dodecyl-3-methylimidazolium tetracyanoborate.

The advantage of the ionic liquid (IL) containing a tetracyanoborate anion, for example DMIM TCB, over oleyl alcohol (OA) is that the ionic liquid is able to extract butanol and acetone in parallel without restricting the distribution coefficient for butanol. This is confirmed in Examples 2 and 3. Oleyl alcohol is not capable of extracting acetone to a significant extent. If the extraction is carried out with OA and at the same time acetone is present in the aqueous phase, the proportion of extracted butanol is reduced, i.e. the distribution coefficient for butanol is reduced by the presence of acetone.

Acetone and butanol can be separated from one another by distillation from the resultant IL phase comprising the two components, and the two valuable products acetone and butanol can be recovered. On use of oleyl alcohol, acetone cannot be recycled. FIG. 7 shows a comparison of the distribution coefficients for butanol of DMIM TCB compared with oeyl alcohol for butanol/water (one), acetone/butanol/water (two) and acetone/butanol/ethanol (1% by weight, 2% by weight, 0.3% by weight, three) at 25° C. (see Example 6). The bar on the left in each case corresponds to DMIM TCB, the bar on the right to oleyl alcohol. The numbers one, two and three indicate the number of components.

It goes without saying to the person skilled in the art that substituents, such as, for example, C, H, N, O, Cl, F, in the compounds according to the invention can be replaced by the corresponding isotopes.

The provision of the aqueous solution comprising at least one alcohol in the method according to the invention is part of general expert knowledge. It is possible either to prepare the aqueous solution specifically or to employ an aqueous solution from a production process. In the particular case of the fermentation broth, the production process is a fermentation.

Intensive mixing can preferably be carried out with stirring. However, all other types of mixing are also possible, for example physical processes, such as shaking or ultrasound.

The separation of the at least single-phase mixture from step b) of the method according to the invention from the aqueous solution is carried out by methods which are known to the person skilled in the art If the method according to the invention is used in batch operation, separation of the aqueous solution from the at least single-phase mixture comprising at least some of the alcohol to be extracted, as defined above, occurs after completion of the stirring, and the at least one ionic liquid and the lower phase can be separated off, for example, by removal at the bottom of the reaction vessel.

In the case of continuous use of the method, some of the lower phase is likewise taken off continuously at the bottom of the reaction vessel. Reference is made, in particular, to the expert knowledge documented by, for example, the specialist literature by J. Rydberg, M. Cox, C. Muskas, G. R. Chopppin, 2004, Solvent Extraction Principles and Practice or R. H. Perry, 1984, Perry's chemical engineer's handbook.

The lower phase in this separation process is generally the at least multi-phase mixture of the at least one ionic liquid with the extracted part of the alcohol, as described above.

The alcohol component is separated off from the ionic liquid by methods which are known to the person skilled in the art, for example by distillation of the alcohol, stripping, flash, evaporation, adsorption or chromatographic methods.

The treated ionic liquid, as described above, can optionally be fed back into the method according to the invention and is available again as solvent.

The method according to the invention for liquid-liquid extraction can be carried out in continuous, but also in semi-continuous operation, as described above. The purification of the liquid-liquid extraction can be carried out both in-situ and also decoupled. The in-situ extraction involves simultaneous fermentation and separation-off of the valuable product, here in accordance with the invention at least one alcohol, as described above, by bringing the fermentation broth into direct contact with the ionic, liquid. The valuable product is thus removed from the aqueous phase, and the concentration of the valuable product is kept low, so that it does not inhibit the microorganisms. Inhibition means that the growth of the microorganisms is slowed or even stopped, also causing production of the valuable product to be slowed or even stopped.

The method according to the invention, as described above, can be carried out in any suitable apparatus, as are known to the person skilled in the art.

The invention likewise relates to the use of at least one ionic liquid containing tetracyanoborate anions as solvent for a liquid-liquid extraction of alcohols from aqueous solutions.

All comments regarding the preferred embodiments of the method of liquid-liquid extraction, the aqueous solution, the alcohol and the at least one ionic liquid likewise apply to this subject-matter of the invention.

Preferred feature combinations of the invention are disclosed in the claims.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

The ionic liquids containing tetracyanoborate anions can be synthesised, for example, in accordance with the disclosure of WO 2004/072089 ("Salts containing cyanoborate anions", Merck Patent GmbH) or are commercially available.

Examples of the synthesis of selected compounds are:

Example A

Synthesis of trihexyltetradecylammonium tetracyanoborate as Illustrated in FIG. 8

100 g of trihexyltetradecylammonium bromide are dissolved in 400 l of demineralised water, and 31 g of potassium tetracyanoborate are subsequently added slowly. 2 phases slowly form. This two-phase mixture is stirred at room temperature for a further 2 hours (h) and left to stand over-night.

The work-up is carried out by extraction with dichloromethane. The organic phase is then washed free of bromide using demineralised water. 8 g of ALOX and 5 g of activated carbon are added to the organic solution, which is then filtered and subsequently evaporated in a rotary evaporator with a water bath at about 80° C., giving a clear, yellowish, viscous liquid.

Example B

Synthesis of trihexyltetradecylphosphonium tetracyanoborate as Illustrated in FIG. 9

Analogously to Example A, 33 g of potassium tetracyanoborate are added to 100 g of trihexyltetradecylphosphonium chloride, and the mixture is subjected to corresponding work-up, giving a clear, yellowish, viscous liquid.

Example C

Synthesis of 1-methyl-1-octylpyrrolidinium tetracyanoborate as Illustrated in FIG. 10

Analogously to Example A, 61 g of potassium tetracyanoborate are added to 100 g of 1-methyl-1-octylpyrrolidinium bromide, and the mixture is subjected to corresponding work-up, giving a clear, yellowish, viscous liquid.

1H NMR (d6-DMSO): $\delta$=3.42 (m, 4H), 3.27 (m, 4H), 2.97 (s, 3H), 2.50 (m, 2H) 1.69 (m, 2H), 1.23 (m, 10H), 0.87 (t, J(H, H)=7.1 Hz, 3H).

Example D

Synthesis of N-methyl-N-octylmorpholinium tetracyanoborate as Illustrated in FIG. 11

Analogously to Example A, 58 g of potassium tetracyanoborate are added to 100 g of 4-methyl-4-octylmorpholinium bromide, and the mixture is subjected to corresponding work-up, giving a clear, yellowish, viscous liquid.

1H NMR (d6-DMSO): $\delta$=3.90 (m, 4H), 3.39 (m, 6H), 3.10 (s, 3H), 1.67 (m, 2H), 1.29 (m, 10H), 0.87 (t, J(H, H)=7.2 Hz, 3H).

Example E

Synthesis of 1-methyl-1-octylpiperidinium tetracyanoborate as Illustrated in FIG. 12

Analogously to Example A, 58 g of potassium tetracyanoborate are added to 100 g of 1-methyl-1-octylpiperidinium bromide, and the mixture is subjected to corresponding work-up, giving a clear, yellowish, viscous liquid.

1H NMR (d6-DMSO): $\delta$=3.35 (m, 6H), 3.29 (m, 6H), 2.98 (s, 3H), 1.78 (m, 2H), 1.30 (m, 10H), 0.89 (t, J(H, H)=7.2 Hz, 3H).

Example F

Synthesis of 1-octyl-3-methylimidazolium tetracyanoborate as Illustrated in FIG. 13

Analogously to Example A, 183 g of potassium tetracyanoborate are added to 250 g of 3-methyl-1-octylimidazolium chloride, and the mixture is subjected to corresponding work-up, giving a clear, slightly yellowish liquid.

1H NMR (d6-DMSO): $\delta$=9.10 (s, 1H), 7.69 (t, J(H, H)=1.8 Hz, 1H), 7.63 (t, J(H, H)=1.8 Hz, 1H), 4.16 (t, J(H, H)=7.4 Hz, 2H), 3.86 (s, 3H), 1,81 (m, 2H), 1.29 (m, 10H), 0.87 (t, J(H, H)=6.9 Hz, 3H).

Example G

Synthesis of N-octylpyridinium tetracyanoborate as Illustrated in FIG. 14

Analogously to Example A, 83 g of potassium tetracyanoborate are added to 134 g of 1-octylpyridinium bromide, and the mixture is subjected to corresponding work-up, giving a clear, yellowish, viscous liquid.

1H NMR (d6-DMSO): $\delta$=9.09 (m, 2H), 8.61 (m, 1H), 8.16 (m, 2H), 4.60 (t, J(H, H)=7.5 Hz, 2H), 3.31 (m, 2H), 2.5o (m, 2H), 1.93 (m, 2H), 1.23 (m, 6H), 1.23 (t, J(H, H)=7.2 Hz, 3H).

Example 1

Procedure:

The distribution coefficient is measured in double-walled glass vessels having a maximum volume of 10 ml. The initial concentration of butanol in the aqueous phase is 1% by weight. Equal weights (3 g) of each phase are brought into contact and mixed intensively by means of a magnetic stirrer (Variomag telesystem 06.07) at constant temperature (25° C.) for 24 h. The long experimental duration means that the achievement of equilibrium is ensured. The temperature control is carried out by means of a cryostat (Julabo F25 ME). After phase separation for 10 minutes, samples of each phase are taken and analysed.

The results for ionic liquids [1] to [7], as listed below, are shown graphically in FIG. 3.

The selectivity S for n-butanol over water is plotted against the distribution coefficient D of n-butanol. All ionic liquids investigated have a distribution coefficient of greater than or equal to 2, and the selectivities are all greater than 73. The results therefore confirm the particular suitability as solvent for n-butanol from aqueous solutions.

Ionic liquids [1] and [2] exhibit more hydrophobic behaviour owing to the longer alkyl chains and thus have much higher selectivities compared with the other ionic liquids investigated ionic liquids [3] and [7] exhibit virtually identical distribution coefficients of 3 and slight differences in the selectivity. Ionic liquid [6] has the highest and thus best distribution coefficient of 3.7 and a selectivity of 97.

The substance currently most investigated, oleyl alcohol, achieved a distribution coefficient of 3.4 and a selectivity of 208 in this investigation.

[1] trihexyltetradecylammonium tetracyanoborate
[2] trihexyltetradecylphosphonium tetracyanoborate
[3] 1-methyl-1-octylpyrrolidinium tetracyanoborate
[4] N-octyl-N-methylmorpholinium tetracyanoborate
[5] 1-methyl-1-octylpiperidinium tetracyanoborate
[6] 1-octyl-3-methylimidazolium tetracyanoborate
[7] 1-octylpyridinium tetracyanoborate Example 2

The distribution coefficients are measured in double-walled glass vessels having a maximum volume of 10 ml. Two different aqueous phases are employed. Besides water, aqueous phase A comprises only the component butanol in a concentration of 2% by weight. Aqueous phase B additionally also comprises the component acetone. The initial concentrations of this phase B are 2% by weight of butanol and 1%, by weight of acetone. The IL 1-decyl-3-methylimidazolium tetracyanoborate is investigated. Equal weights (3 g) of each phase are brought into contact and mixed intensively by means of a magnetic stirrer (Variomag telesystem 06.07) at constant temperature (25° C.) for 24 h. The temperature control is carried out by means of a cryostat (Julabo F25 ME). After phase separation for 10 minutes, samples of each phase are taken and analysed.

The selectivity S over water is not affected by the presence of the further component acetone. The selectivity S for n-butanol over water is 104 for aqueous phase A and 100 for aqueous phase B.

The distribution coefficient D of n-butanol on extraction from aqueous phase A is 3.27. The distribution coefficient D of n-butanol on extraction from aqueous phase B is 3.23 and that of acetone is 2.36.

These results show that the distribution coefficient D of n-butanol is not affected by the presence of a further component such as acetone. The distribution coefficient D of acetone in the presence of butanol shows that acetone is also extracted by the ionic liquid 1-decyl-3-methylimidazolium tetracyanoborate (DMIM TCB), but significantly less than butanol. The ionic liquid 1-decyl-3-methylimidazolium tetracyanoborate is accordingly able to separate off n-butanol more selectively.

Example 3

Analogously to Example 2, an aqueous phase comprising 2% by weight of n-butanol, 1% by weight of acetone and 0.3% by weight of ethanol is investigated at a temperature of 20° C. The distribution coefficient D of n-butanol at 20° C. from the aqueous phase for the ionic liquid 1-decyl-3-methylimidazolium tetracyanoborate is 3.04. The extraction of n-butanol in the presence of acetone and ethanol is not impaired and is thus possible in a selective manner.

Examples 2 and 3 support the method according to the invention for a two-component or three-component system, i.e. simple systems of a synthetic fermentation broth of an ABE fermentation.

Example 4

Investigations of the Initial Concentration of Butanol and the Temperature

The effect of the temperature and the initial Concentration of butanol, is investigated using the ionic liquid 1-decyl-3-methylimidazolium tetracyanoborate. The distribution coefficient is measured in double-walled glass vessels having a maximum volume of 10 ml, and equal weights (3 g) of each phase are investigated. The initial concentration of butanol in the aqueous phase varies between 0.2 and 2% by weight. The temperatures are varied between 20° C. and 40° C. in steps of 5° C. These are standard conditions of a fermentation. The equal weights (3 g) of each phase are brought into contact and mixed intensively by means of a magnetic stirrer (Variomag telesystem 06.07). The temperature investigated in each case is kept constant by a thermostatic circulating water bath (Julabo F25 ME). After phase separation for 10 minutes, samples of each phase are taken and analysed.

Evaluation:

The distribution coefficient increases from 2.6 to 3.3 with increasing initial butanol concentration in the aqueous phase at a constant temperature of 25° C. At the measured temperatures (20° C., 25° C., 30° C., 35° C., 40° C.), the distribution coefficient increases by 0.6 to 1 with increasing initial concentration of butanol. The higher the temperature of the extraction, the smaller the increase in the distribution coefficient.

The distribution coefficient increases from 2.7 to 4.3 with increasing temperature and constant initial concentration of butanol in the aqueous phase of 1% by weight. An increase of between 1.4 and 3.0 in the distribution coefficient is obtained at each measured initial concentration of butanol.

FIG. 4 summarises this result and describes the effect of temperature and initial concentration on the distribution coefficient of butanol in the DMIM TCB/water system.

An increase in the selectivity for butanol over water at a constant temperature of 25° C. with increasing initial concentration from 87 to 107 is likewise observed. The selectivity increases from 100 to 133 with an increase in the temperature and constant initial concentration of butanol in the aqueous phase of 1% by weight. An increase of between 28 and 50 in the selectivity is obtained at each measured initial concentration of butanol.

FIG. 5 summarises this result and describes the effect of temperature and initial concentration on the selectivity for butanol over water in the DMIM TCB/water system.

FIG. 6 shows the effect of the temperature on the selectivity for butanol over water, plotted against the distribution coefficient of butanol in the DMIM TCB/water system for 1% by weight of butanol in the aqueous solution compared with oleyl alcohol at 25° C.

Example 5

Settling Time and Phase Separation

Equal volumes (3 ml) of water and the ionic liquid 1-decyl-3-methylimidazolium tetracyanoborate or of water and oleyl alcohol are brought into contact and mixed intensively. After completion of the mixing, the time for phase separation is measured. After 15 minutes, a clear phase separation in the ionic liquid (IL)/water system is obtained, and the IL phase has formed to the extent of 90%.

The oleyl alcohol phase has only formed to the extent of 35% after 15 minutes, to the extent of 45% after 20 minutes and to the extent of 90% after 25 minutes.

The settling time of the IL/water system accordingly requires only half the time compared with the oleyl alcohol/water system.

Example 6

Comparison with Oleyl Alcohol

As described above, small amounts of polar by-products, such as ethanol or acetone, are found in the fermentation broth. It is therefore relevant also to check the performance of the extractant in the presence of these by-products (see also Examples 2 and 3).

Comparison of DMIM TCB with oleyl alcohol:

The distribution coefficient is measured in double-walled glass vessels having a maximum volume of 10 ml, and equal weights (3 g) of DMIM TCB or oleyl alcohol are investigated.

Three solutions are investigated:

Solution A comprising 2 per cent by weight of butanol (one component);

Solution B comprising 2 per cent by weight of butanol and 1 per cent by weight of acetone (two components);

Solution C comprising 2 per cent by weight of butanol, 1 per cent by weight of acetone and 0.3 per cent by weight of ethanol.

The equal weights (3 g) are brought into contact with the respective solution and mixed intensively by means of a magnetic stirrer (Variomag telesystem 06.07). The temperature is kept constant by a thermostatic circulating water bath (Julabo F25 ME) at 25° C. for 24 h. After phase separation for 10 minutes, samples of each phase are taken and analysed.

For solution A, the distribution coefficient of butanol is 3.2 for DMIM TCB and 4.0 for oleyl alcohol (OA).

For solution B, the distribution coefficient of butanol has risen to 3.5 for DMIM TCB, while the distribution coefficient of butanol drops to 4.0 for OA. For solution C, the distribution coefficient of butanol for DMIM TCB is in statistical terms comparable to the value for OA. FIG. 7 illustrates this result.

The presence of polar components, such as, for example, acetone or ethanol, improves the performance of DMIM TCB. The same polar components cause a decrease in the performance of oleyl alcohol.

Figure 1:
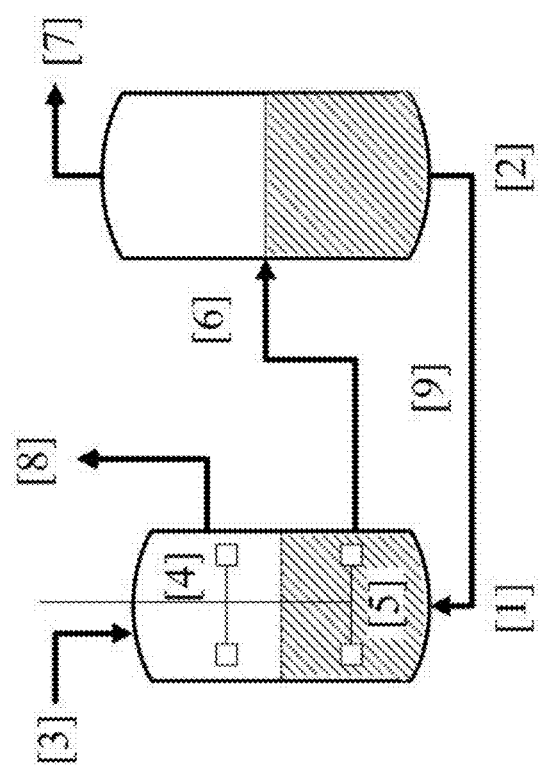
FIG. 1: Variant of a liquid-liquid extraction.
Figure 2:
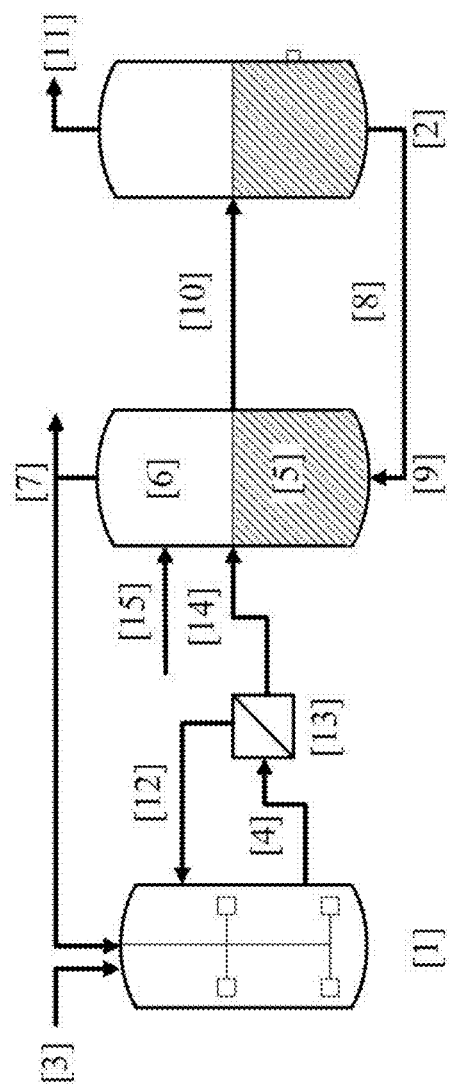
FIG. 2: Fermentation with the aid of an extraction column.
Figure 3:
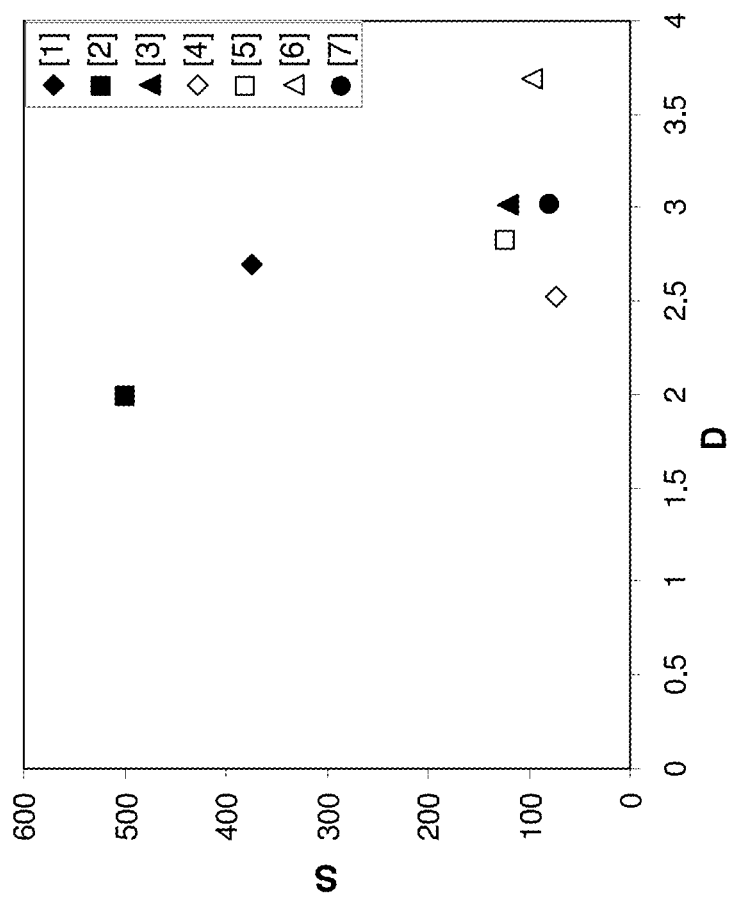
FIG. 3: Selectivity S for n-butanol over water is plotted against the distribution coefficient D of n-butanol.
Figure 4:
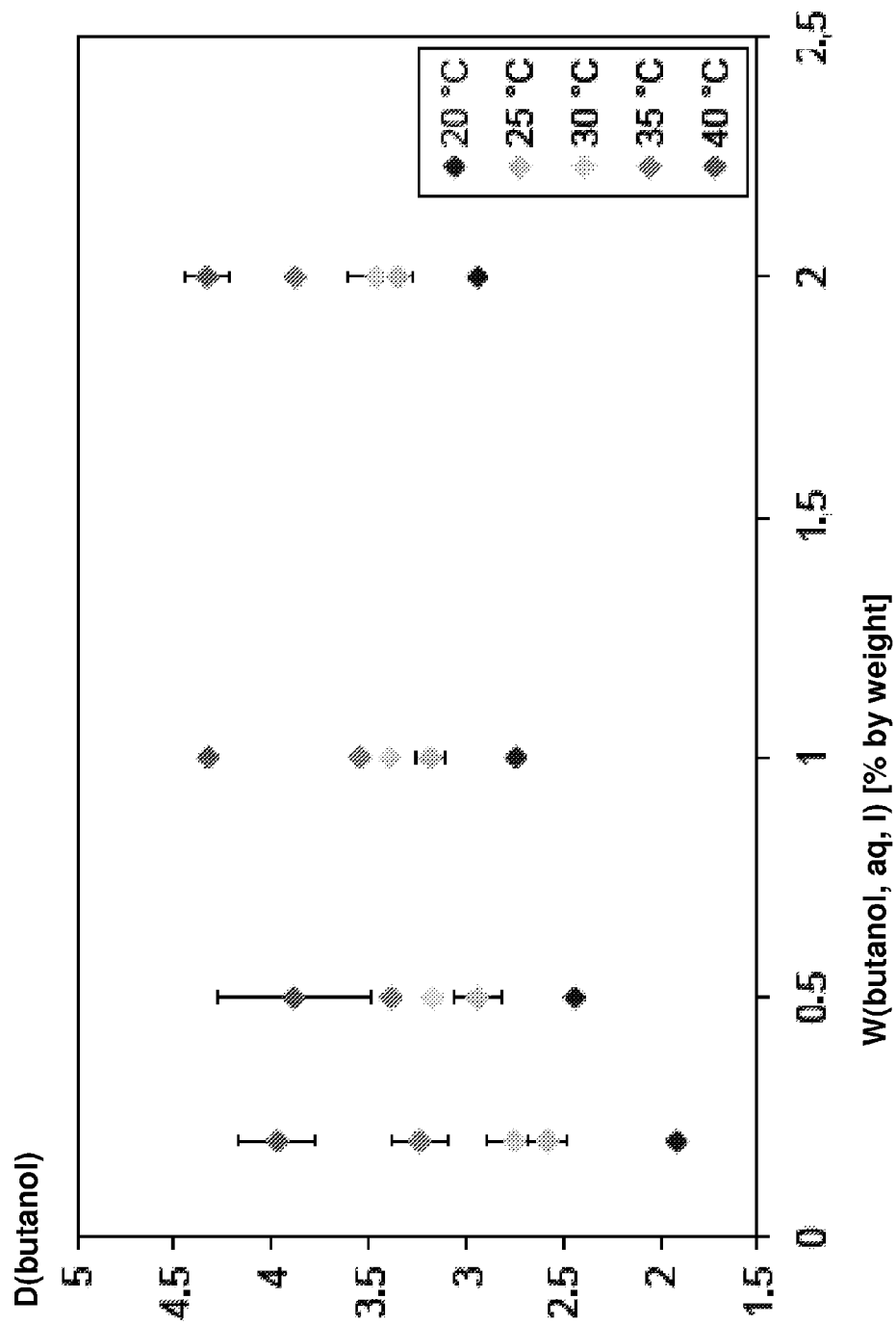
FIG. 4: Effect of temperature and initial concentration on the distribution coefficient D of butanol in the DMIM TCB/water system.
Figure 5:
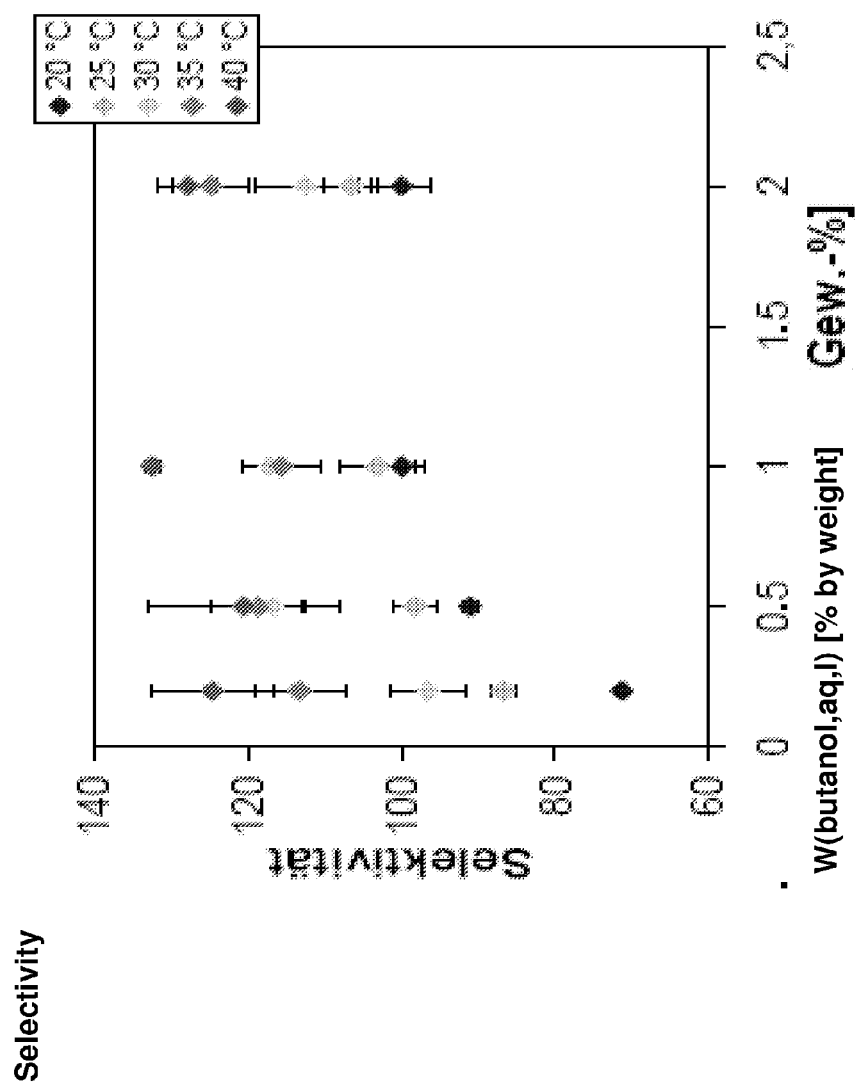
FIG. 5: Effect of temperature and initial concentration on the selectivity for butanol over water in the DMIM TCB/water system.
Figure 6:
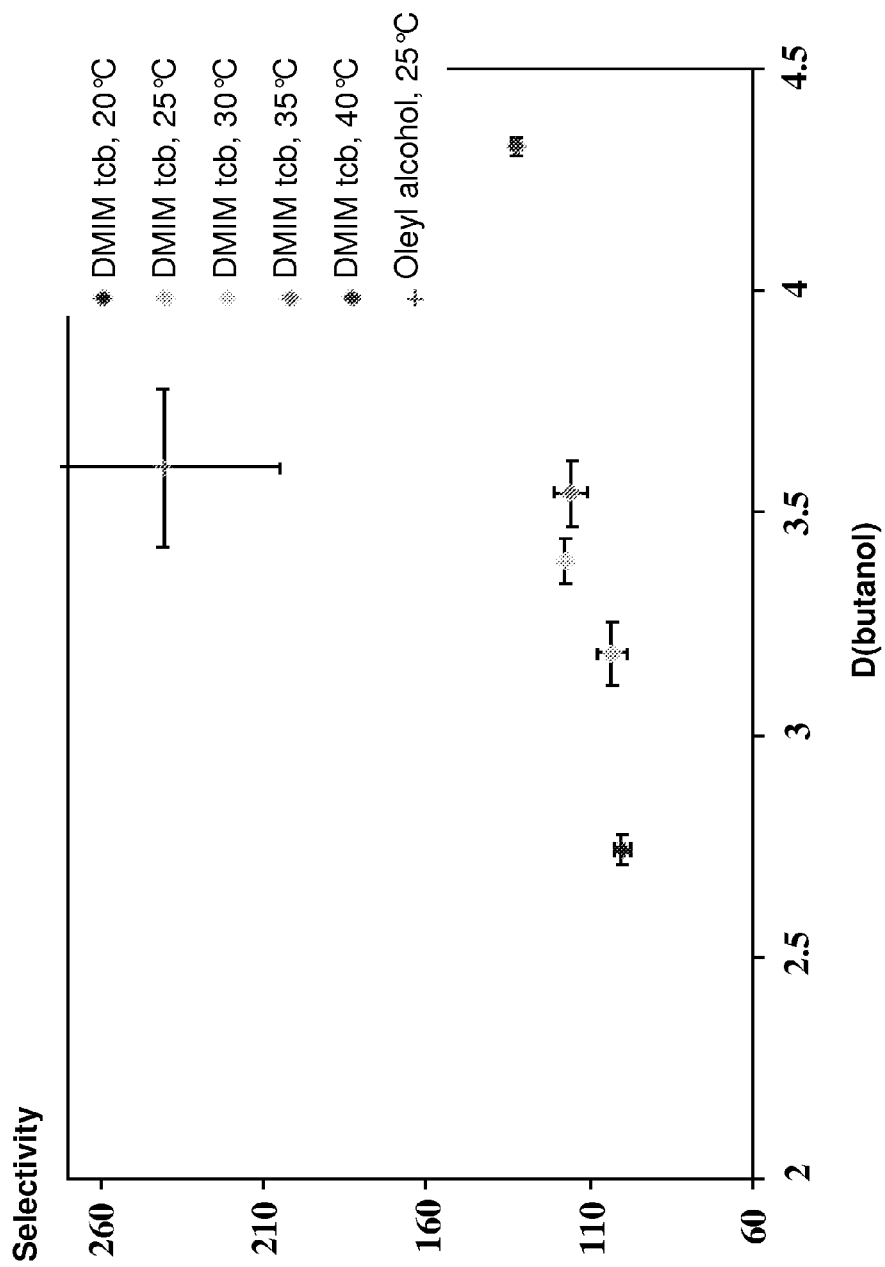
FIG. 6: Effect of temperature on the selectivity for butanol over water plotted against the distribution coefficient D of butanol in the DMIM TCB/water system with a 1% by weight initial concentration of butanol.
Figure 7:
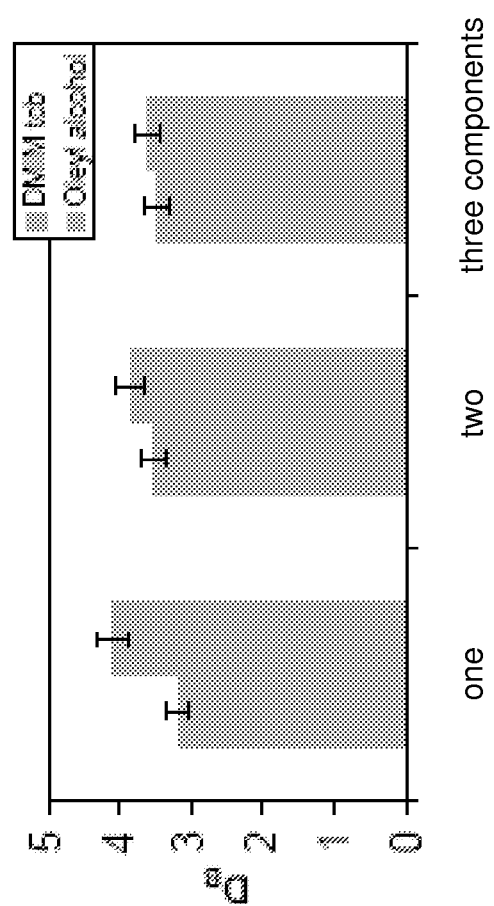
FIG. 7: Comparison of the distribution coefficients for butanol of DMIM TCB compared with oleyl alcohol for butanol/water (one), acetone/butanol/water (two) and acetone/butanol/ethanol (1% by weight, 2% by weight, 0.3% by weight; three) at 25° C.
Figure 8:
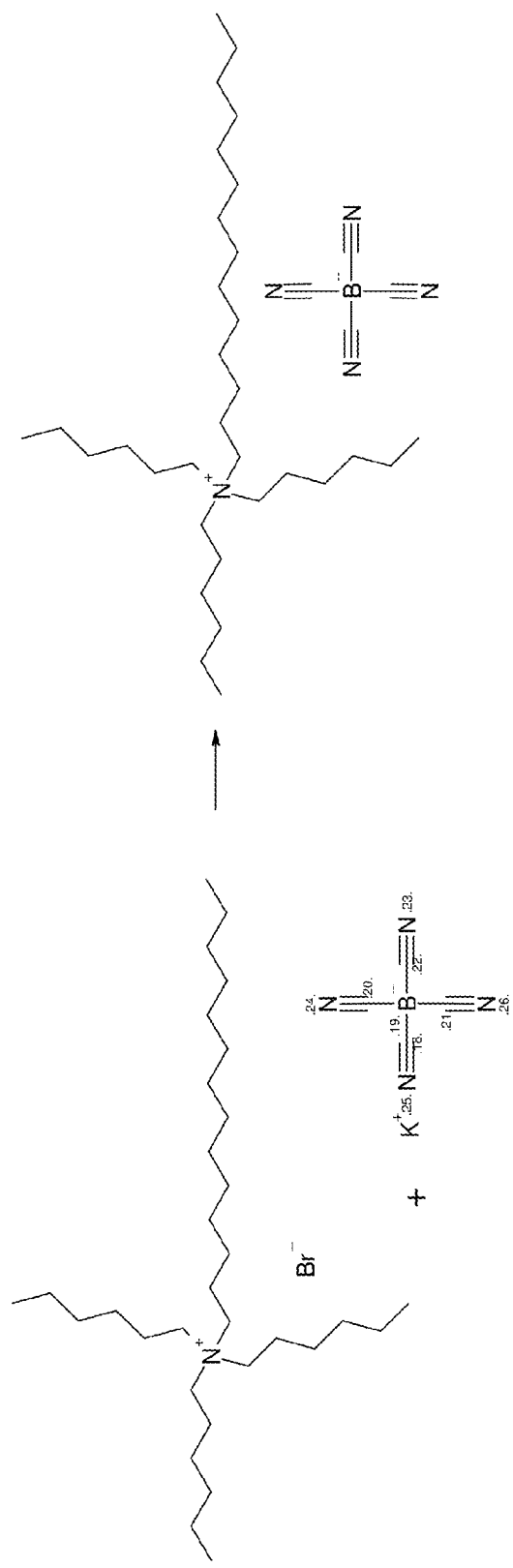
FIG. 8: Synthesis of trihexyltetradecylammonium tetracyanoborate.
Figure 9:
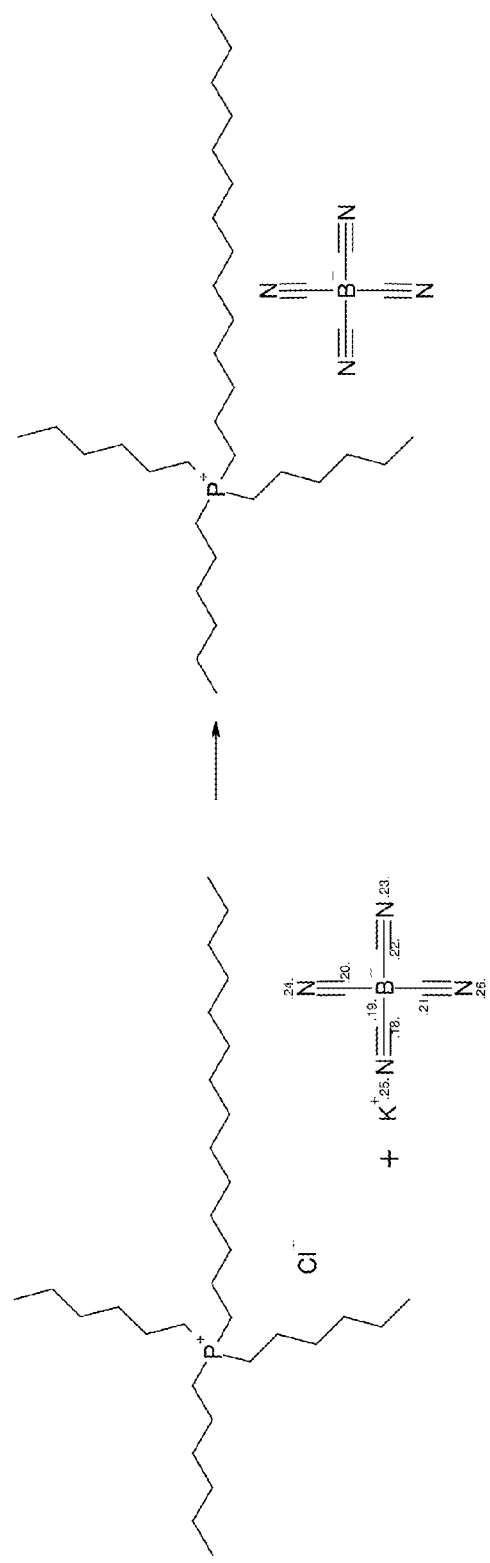
FIG. 9: Synthesis of trihexyltetradecylphosphonium tetracyanoborate.
Figure 10:
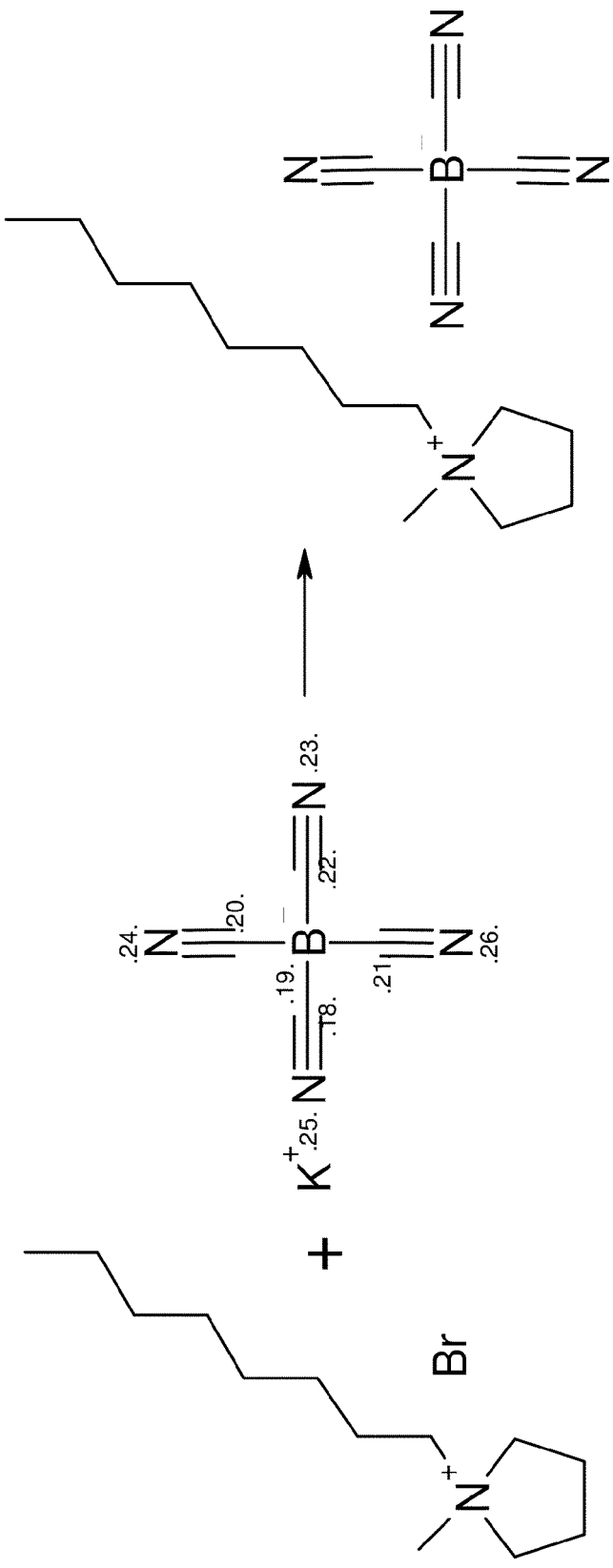
FIG. 10: Synthesis of 1-methyl-1-octylpyrrolidinium tetracyanoborate.
Figure 11:
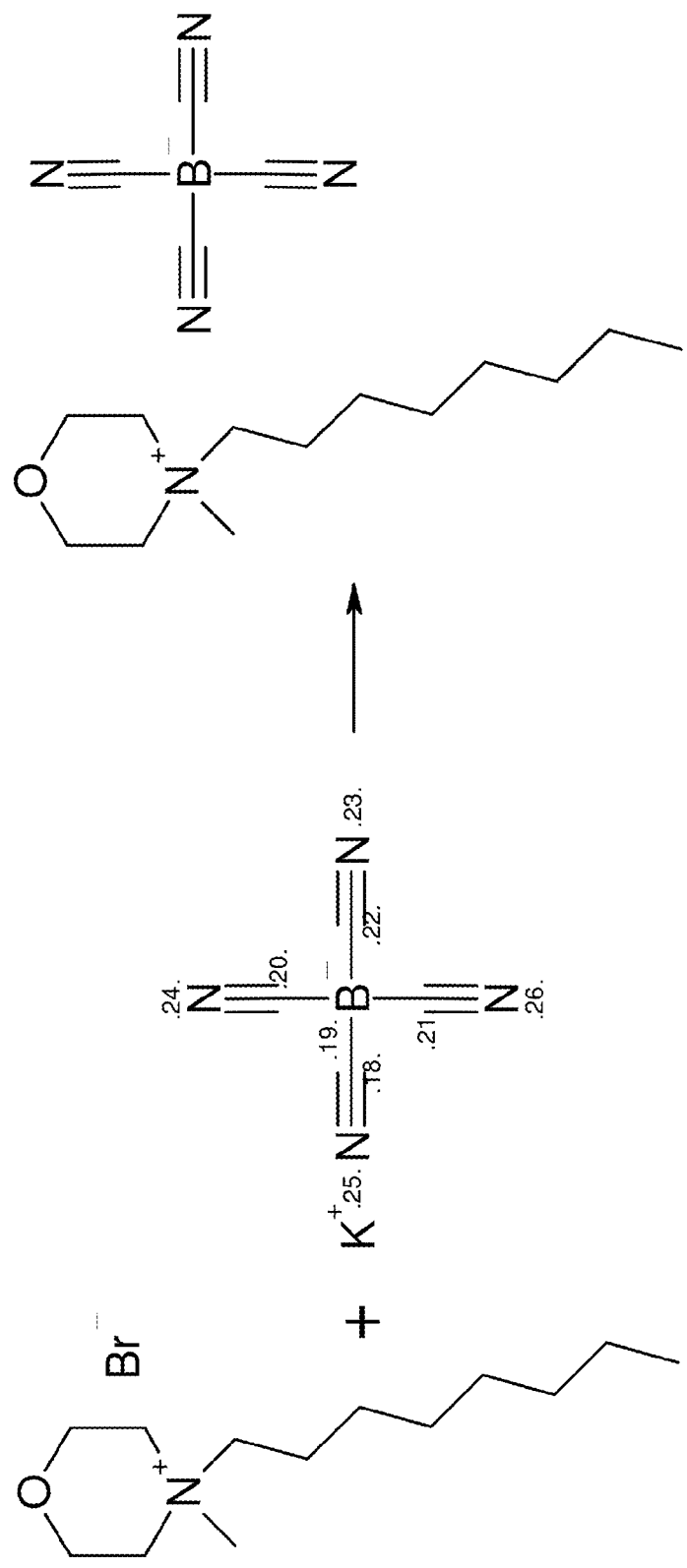
FIG. 11: Synthesis of N-methyl-N-octylmorpholinium tetracyanoborate.
Figure 12:
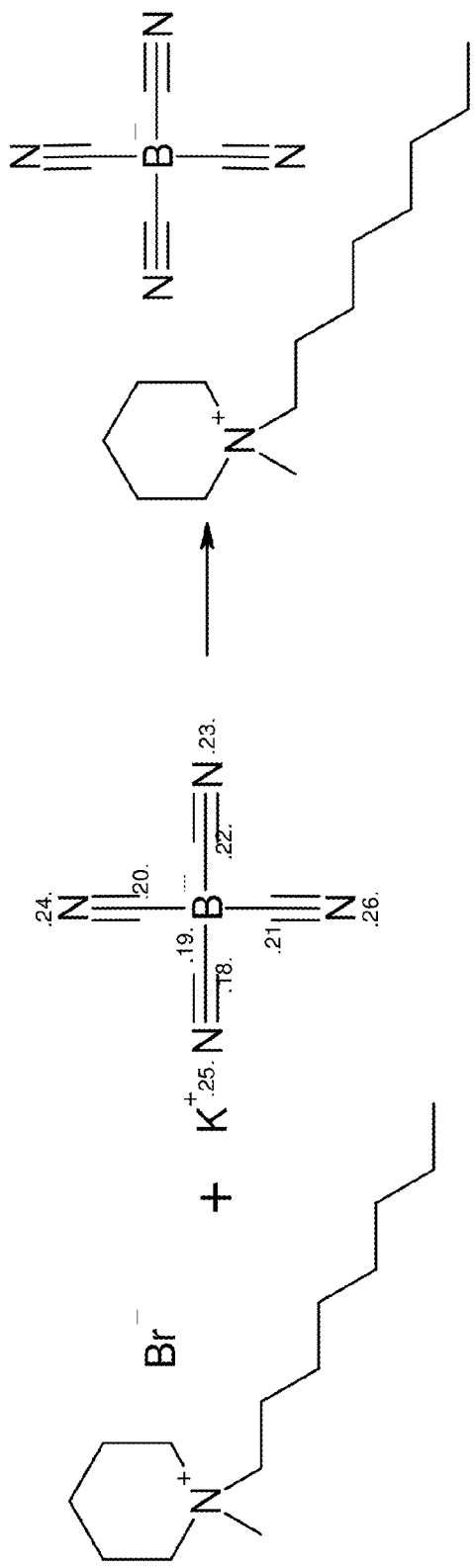
FIG. 12: Synthesis of 1-methyl-1-octylpiperidinium tetracyanoborate.
Figure 13:
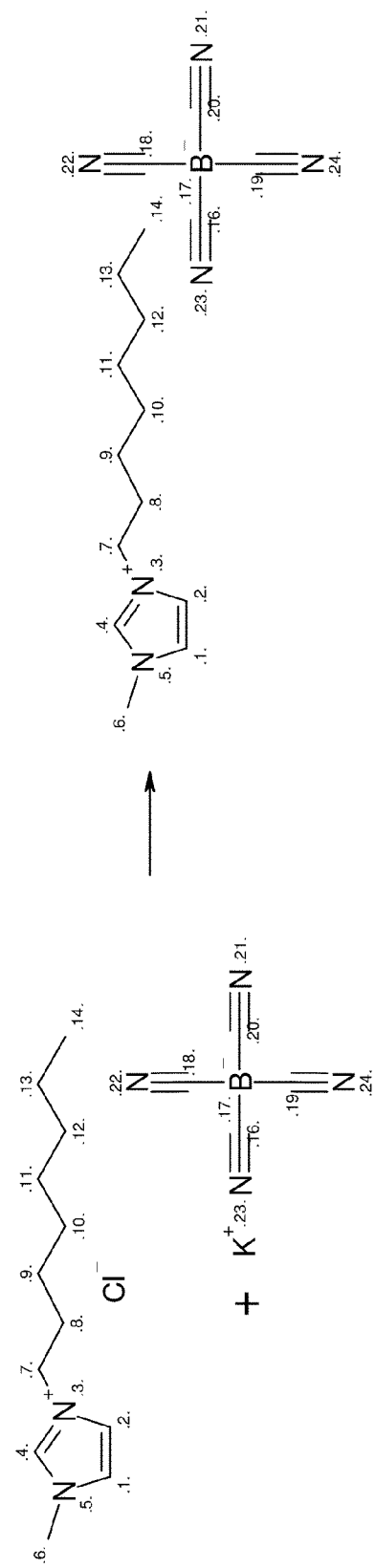
FIG. 13: Synthesis of 1-octyl-3-methylimidazolium tetracyanoborate.
Figure 14:
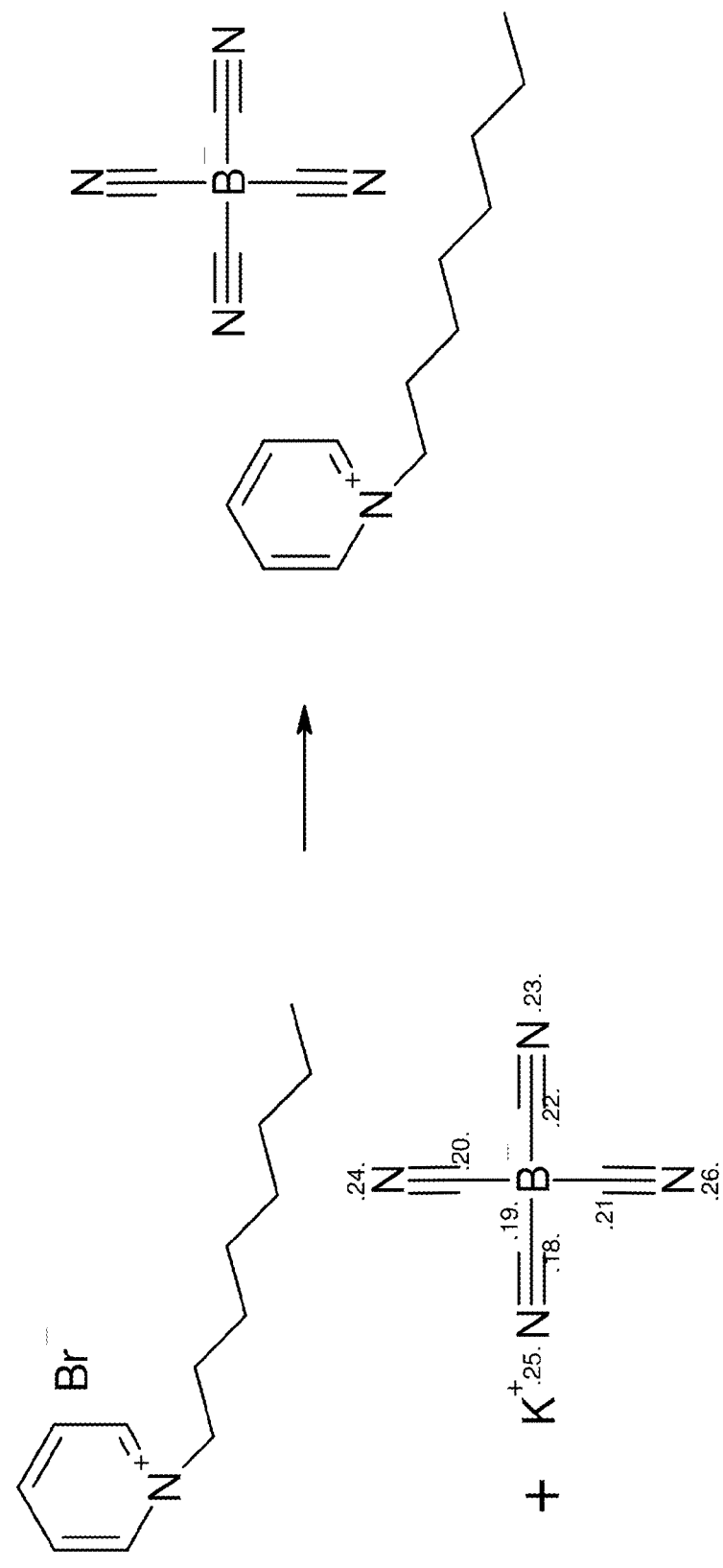
FIG. 14: Synthesis of N-octylpyridinium tetracyanoborate.

The invention claimed is:

1. A method for liquid-liquid extracting an alcohol from an aqueous solution, comprising liquid-liquid extracting an alcohol from an aqueous solution by at least one ionic liquid containing tetracyanoborate anions as solvent.

2. A method according to claim 1, wherein the ionic liquid containing tetracyanoborate anions forms one two-phase mixture with the aqueous solution comprising the alcohol.

3. A method according to claim 1, comprising
   a) providing an aqueous solution comprising at least one alcohol,
   b) effectively mixing the aqueous solution from a) with the at least one ionic liquid containing tetracyanoborate anions, as a result of which mixing the ionic liquid is able to extract at least some of the alcohol from the aqueous solution and form a single-phase mixture with the extracted alcohol,
   c) separating off the single-phase mixture from b) from the aqueous solution,
   d) separating the single-phase mixture from c) into the components alcohol and ionic liquid, and optionally
   e) feeding back the ionic liquid from d) into b).

4. A method according to claim 1, which is carried out continuously or semi-continuously.

5. A method according to claim 1, wherein the alcohol is ethanol, isopropanol, propanol, n-butanol or an isomer of n-butanol, or a mixture thereof.

6. A method according to claim 5, wherein the alcohol is n-butanol.

7. A method according to claim 1, wherein the aqueous solution comprising the alcohol is a fermentation broth.

8. A method according to claim 7, wherein the fermentation broth originates from an acetone-butanol-ethanol fermentation.

9. A method according to claim 1, wherein the at least one ionic liquid containing tetracyanoborate anions comprises a compound of formula (1), (2) or (3)

(1),

(2),

(3), where
R in each case, independently of one another, denotes
- a straight-chain or branched alkyl having 1-20 C atoms,
- a straight-chain or branched alkenyl having 2-20 C atoms and one or more double bonds,
- a straight-chain or branched alkynyl having 2-20 C atoms and one or more triple bonds,
- a saturated, partially or fully unsaturated cycloalkyl having 5-7 C atoms, which is optionally substituted by one or more alkyl groups having 1-6 C atoms, with the proviso that at least two substituents R have at least 5 C atoms.

10. A method according to claim 1, wherein the at least one ionic liquid containing tetracyanoborate anions comprises a compound of formula (4) or (5)

$$[C(R^3R^4N)(OR^5)(NR^6R^7)]^+[B(CN)_4]^- \quad (4),$$

$$[C(R^3R^4N)(SR^5)(NR^6R^7)]^+[B(CN)_4]^- \quad (5),$$

where
$R^3$ to $R^7$ each, independently of one another, denote
H, where H is excluded for $R^5$,
- a straight-chain or branched alkyl having 1 to 20 C atoms,
- a straight-chain or branched alkenyl having 2-20 C atoms and one or more double bonds,
- a straight-chain or branched alkynyl having 2-20 C atoms and one or more triple bonds,
- a saturated, partially or fully unsaturated cycloalkyl having 3-7 C atoms, which is optionally substituted by one or more alkyl groups having 1-6 C atoms.

11. A method according to claim 1, wherein the at least one ionic liquid containing tetracyanoborate anions comprises a compound of formula (6)

$$[C(NR^8R^9)(NR^{10}R^{11})(NR^{12}R^{13})]^+[B(CN)_4]^- \quad (6),$$

where
$R^8$ to $R^{13}$ each, independently of one another, denote
H,
- a straight-chain or branched alkyl having 1 to 20 C atoms,
- a straight-chain or branched alkenyl having 2-20 C atoms and one or more double bonds,
- a straight-chain or branched alkynyl having 2-20 C atoms and one or more triple bonds,
- a saturated, partially or fully unsaturated cycloalkyl having 3-7 C atoms, which is optionally substituted by one or more alkyl groups having 1-6 C atoms.

12. A method according to claim 1, wherein the at least one ionic liquid containing tetracyanoborate anions comprises a compound of formula (7)

$$[HetN]^{z+}[B(CN)_4]^- \quad (7),$$

where
$HetN^{z+}$ denotes

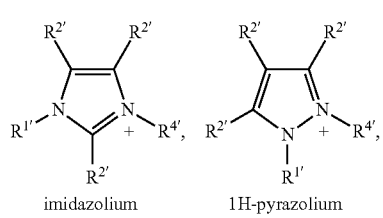

imidazolium, 1H-pyrazolium

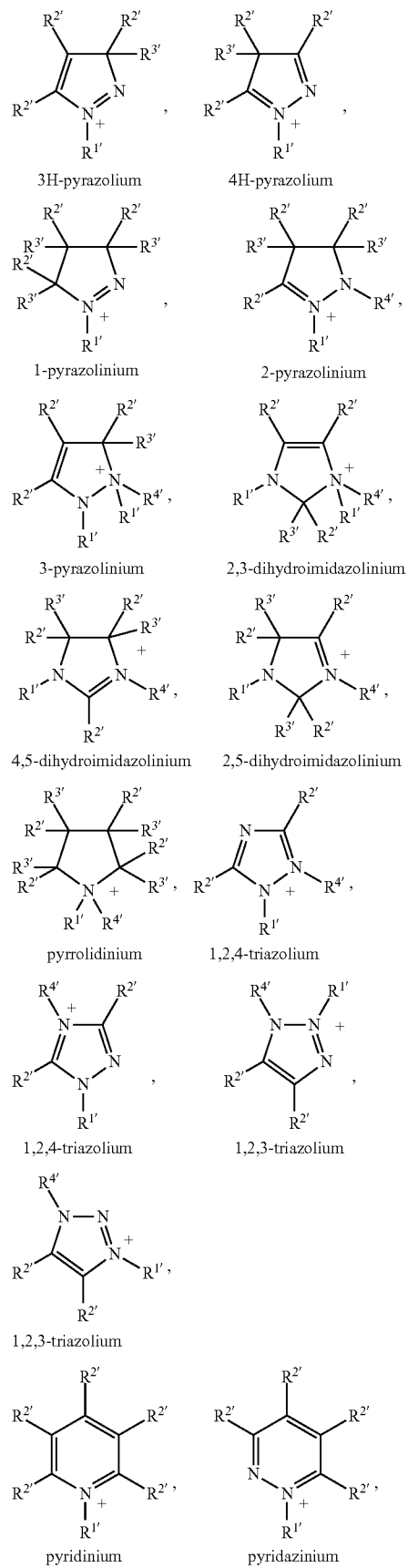

-continued

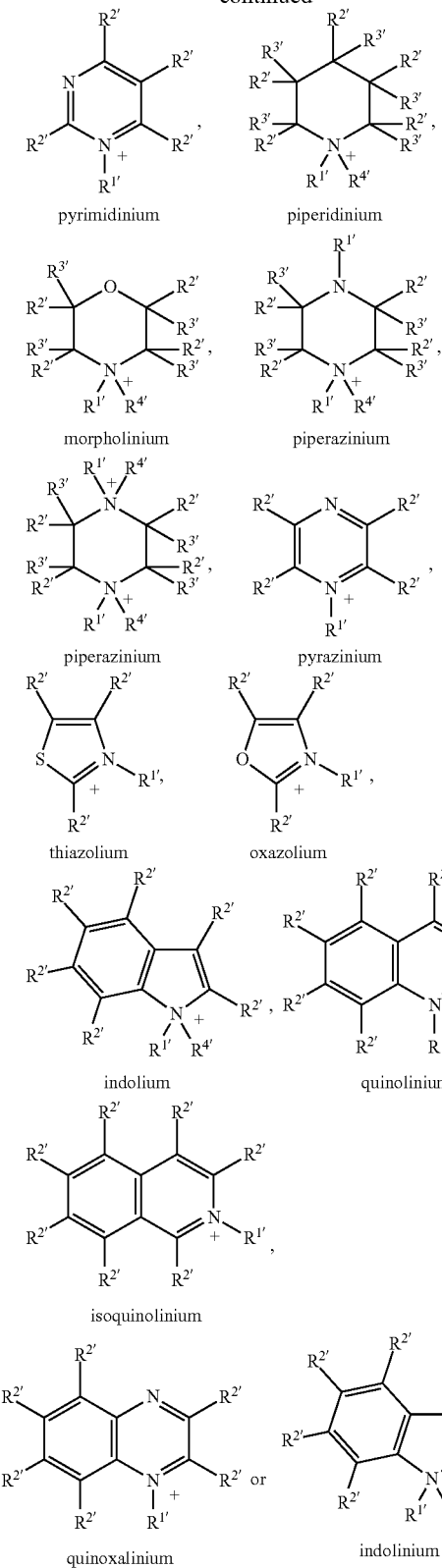

pyrimidinium, piperidinium, morpholinium, piperazinium, piperazinium, pyrazinium, thiazolium, oxazolium, indolium, quinolinium, isoquinolinium, quinoxalinium, indolinium $R^{1'}$ to $R^{4'}$ each, independently of one another, denote
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
a saturated, partially or fully unsaturated cycloalkyl having 5-7 C atoms, which is optionally substituted by one or more alkyl groups having 1-6 C atoms,
or
$R^{1'}$, $R^{2'}$, $R^{3'}$ and/or $R^{4'}$ together form a ring system.

13. A method according to claim 1, wherein the at least one ionic liquid containing tetracyanoborate anions comprises a compound of formula (1), (2) or (7)

$$[NR_4]^+[B(CN)_4]^- \qquad (1),$$

$$[PR_4]^+[B(CN)_4]^- \qquad (2),$$

$$[HetN]^{z+}[B(CN)_4]^- \qquad (7),$$

where
R in each case, independently of one another, denotes
a straight-chain or branched alkyl having 1-20 C atoms,
a straight-chain or branched alkenyl having 2-20 C atoms and one or more double bonds,
a straight-chain or branched alkynyl having 2-20 C atoms and one or more triple bonds,
a saturated, partially or fully unsaturated cycloalkyl having 5-7 C atoms, which is optionally substituted by one or more alkyl groups having 1-6 C atoms, with the proviso that at least two substituents R have at least 5 C atoms,
$HetN^{z+}$ denotes

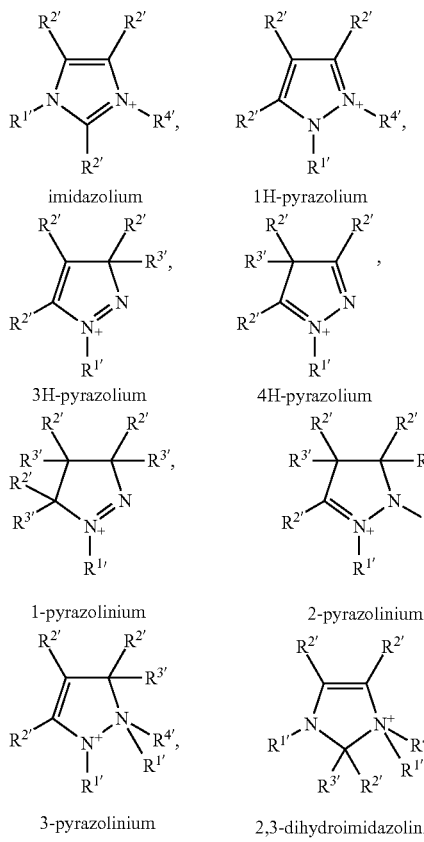

imidazolium, 1H-pyrazolium, 3H-pyrazolium, 4H-pyrazolium, 1-pyrazolinium, 2-pyrazolinium, 3-pyrazolinium, 2,3-dihydroimidazolinium -continued

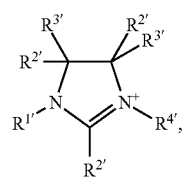
4,5-dihydroimidazolinium

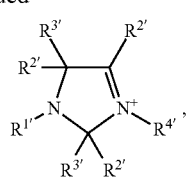
2,5-dihydroimidazolinium

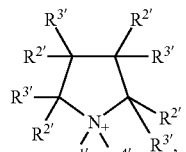
pyrrolidinium

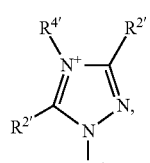
1,2,4-triazolium

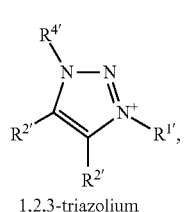
1,2,4-triazolium 1,2,3-triazolium

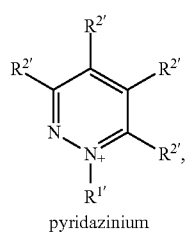
1,2,3-triazolium pyridinium

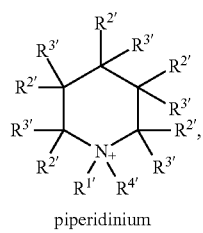
pyridazinium pyrimidinium

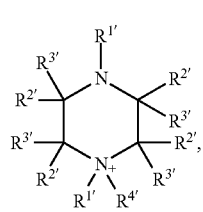
piperidinium

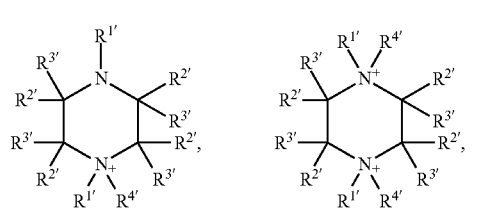
morpholinium

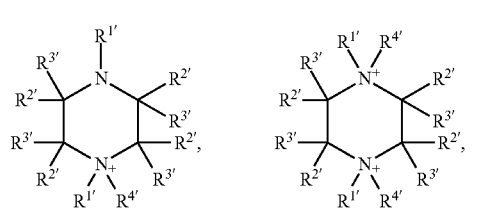
piperazinium      piperazinium

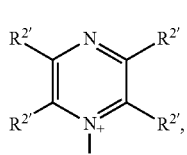
pyrazinium

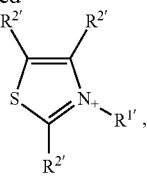
thiazolium

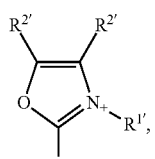
oxazolium

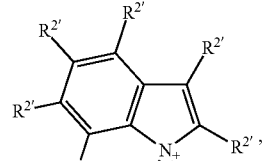
indolium

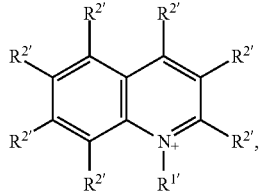
quinolinium

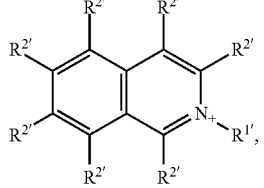
isoquinolinium

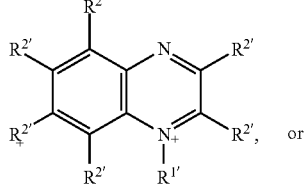
quinoxalinium, or

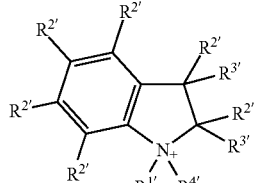
indolinium $R^{1'}$ to $R^{4'}$ each, independently of one another, denote
  a straight-chain or branched alkyl having 1-20 C atoms,
  a straight-chain or branched alkenyl having 2-20 C atoms and one or more double bonds,
  a straight-chain or branched alkynyl having 2-20 C atoms and one or more triple bonds, a saturated, partially or fully unsaturated cycloalkyl having 5-7 C atoms, which is optionally substituted by one or more alkyl groups having 1-6 C atoms,
or $R^{1'}$, $R^{2'}$, $R^{3'}$ and/or $R^{4'}$ together form a ring system.

14. A method according to claim 1, wherein the at least one ionic liquid containing tetracyanoborate anions comprises
1-octyl-3-methylimidazolium tetracyanoborate,
1-decyl-3-methylimidazolium tetracyanoborate,
1-dodecyl-3-methylimidazolium tetracyanoborate,
trihexyltetradecylammonium tetracyanoborate,
trihexyltetradecylphosphonium tetracyanoborate,
N-octylpyridinium tetracyanoborate,
1-octyl-1-methylpyrrolidinium tetracyanoborate,
N-octyl-N-methylmorpholinium tetracyanoborate, or
1-octyl-1-methylpiperidinium tetracyanoborate.

15. An ionic liquid containing tetracyanoborate anions suitable as solvent for a liquid-liquid extraction of an alcohol from an aqueous solution, wherein the liquid further comprises said alcohol.

* * * * *